US008651104B2

(12) United States Patent
Donovan et al.

(10) Patent No.: US 8,651,104 B2
(45) Date of Patent: *Feb. 18, 2014

(54) BEAD-CONTAINING DRY POWDER INHALER

(75) Inventors: Martin J. Donovan, El Paso, TX (US); Jacques Pappo, Austin, TX (US); Hugh Smyth, West Lake Hills, TX (US)

(73) Assignee: Respira Therapeutics, Inc., Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/469,963

(22) Filed: May 11, 2012

(65) Prior Publication Data
US 2012/0291780 A1    Nov. 22, 2012

Related U.S. Application Data

(63) Continuation-in-part of application No. 13/313,778, filed on Dec. 7, 2011.

(60) Provisional application No. 61/442,872, filed on Feb. 15, 2011, provisional application No. 61/420,639, filed on Dec. 7, 2010.

(51) Int. Cl.
*A61M 16/00* (2006.01)
*A61M 15/00* (2006.01)
*B05D 7/14* (2006.01)
*B65D 83/06* (2006.01)

(52) U.S. Cl.
USPC .................................................. 128/203.15

(58) Field of Classification Search
USPC .......................... 128/203.15, 203.19, 203.21
See application file for complete search history.

(56) References Cited

U.S. PATENT DOCUMENTS

| | | |
|---|---|---|
| 16,066 A | 11/1856 | Murphy |
| 361,748 A | 4/1867 | Culbertson |
| 263,451 A | 8/1882 | Adams |
| 376,819 A | 1/1888 | Glew |
| 419,942 A | 1/1890 | Harding |
| 598,286 A | 2/1898 | Curran |
| 631,621 A | 8/1899 | Curran |
| 658,436 A | 9/1900 | Groth |
| 844,097 A | 2/1907 | Caldwell |

(Continued)

FOREIGN PATENT DOCUMENTS

| | | |
|---|---|---|
| EP | 1 291 032 A2 | 3/2003 |
| EP | 1 658 872 A2 | 5/2006 |
| WO | 2006/031775 A2 | 3/2006 |

OTHER PUBLICATIONS

Crowder, T., et al., "2001: An Odyssey in Inhaler Formulation and Design," Pharmaceutical Technology, Jul. 2001, 9 pages.

(Continued)

*Primary Examiner* — Loan H Thanh
*Assistant Examiner* — Jennifer M Deichl
(74) *Attorney, Agent, or Firm* — Kilpatrick Townsend & Stockton LLP

(57) ABSTRACT

A dry powder inhaler includes a chamber holding a bead-like actuator to which a powdered medicament is adhered. Air is drawn into the chamber through an inlet flow channel and exits through an outlet flow channel. The bead-like actuator oscillates in response to the air flow, dislodging powdered medicament to be entrained in the air flow and delivered to the patient.

18 Claims, 11 Drawing Sheets

(56) References Cited

U.S. PATENT DOCUMENTS

Figure 1:
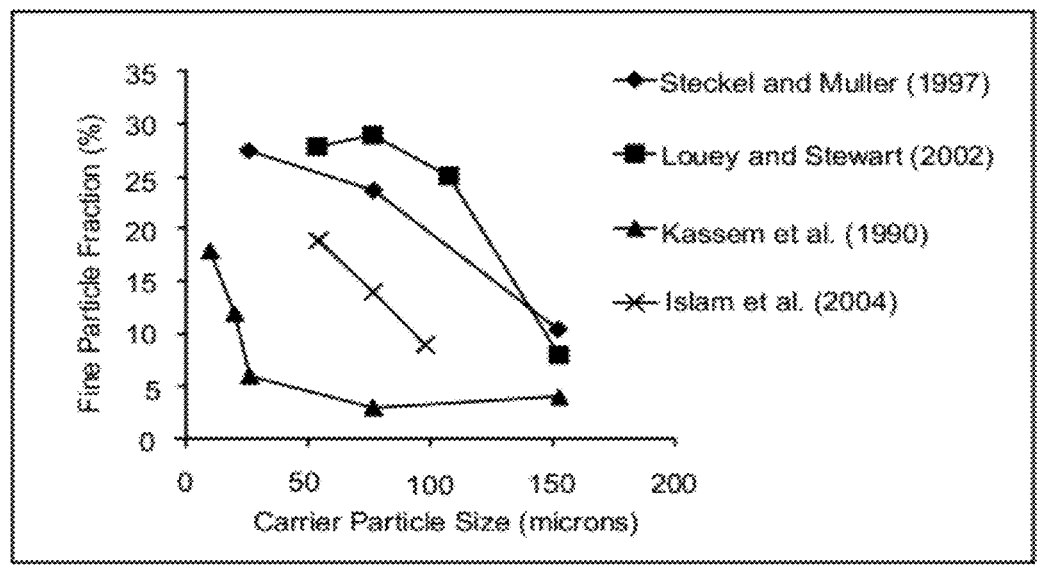

| Patent Number | | Date | Inventor |
|---|---|---|---|
| 1,599,959 | A | 9/1926 | Fujimoto |
| 1,752,956 | A | 4/1930 | Lex |
| 2,214,032 | A | 9/1940 | Stewart |
| 2,470,296 | A | 5/1949 | Fields |
| 2,513,145 | A | 6/1950 | Chapple |
| 2,517,482 | A | 8/1950 | Hall |
| 2,534,636 | A | 12/1950 | Stirn |
| 2,549,303 | A | 4/1951 | Friden |
| 2,573,918 | A | 11/1951 | McCuiston |
| 2,581,182 | A | 1/1952 | Fields |
| 2,587,215 | A | 2/1952 | Priestly |
| 2,603,215 | A | 7/1952 | Arnow |
| 2,603,216 | A | 7/1952 | Taplin et al. |
| 2,622,594 | A | 12/1952 | Brooks |
| 2,641,255 | A | 6/1953 | Leonaitis |
| 2,642,063 | A * | 6/1953 | Brown ............ 128/203.15 |
| 2,672,865 | A | 3/1954 | Willis |
| 2,693,805 | A | 11/1954 | Taplin et al. |
| 2,992,645 | A | 7/1961 | Fowler |
| 3,105,488 | A | 10/1963 | Richards |
| 3,518,992 | A | 7/1970 | Altounyan et al. |
| 3,635,219 | A | 1/1972 | Altounyan et al. |
| 3,807,400 | A | 4/1974 | Cocozza |
| 3,837,341 | A | 9/1974 | Bell |
| 3,858,583 | A | 1/1975 | Hallworth et al. |
| 3,870,046 | A | 3/1975 | Elliott |
| 3,888,252 | A | 6/1975 | Side et al. |
| 3,888,253 | A | 6/1975 | Watt et al. |
| 3,906,950 | A | 9/1975 | Cocozza |
| 3,921,637 | A | 11/1975 | Bennie et al. |
| 3,948,264 | A | 4/1976 | Wilke et al. |
| 3,964,483 | A | 6/1976 | Mathes |
| 3,971,377 | A | 7/1976 | Damani |
| 3,980,074 | A | 9/1976 | Watt et al. |
| 3,991,761 | A | 11/1976 | Cocozza |
| 4,013,075 | A | 3/1977 | Cocozza |
| 4,090,642 | A | 5/1978 | Baker |
| 4,147,166 | A | 4/1979 | Hansen |
| 4,216,768 | A | 8/1980 | Jack |
| 4,338,931 | A | 7/1982 | Cavazza |
| 4,353,365 | A | 10/1982 | Hallworth et al. |
| 4,524,769 | A | 6/1985 | Wetterlin |
| 4,570,630 | A | 2/1986 | Elliott et al. |
| 4,735,358 | A | 4/1988 | Morita et al. |
| 4,841,964 | A | 6/1989 | Hurka et al. |
| 4,860,740 | A | 8/1989 | Kirk et al. |
| 4,907,583 | A | 3/1990 | Wetterlin et al. |
| 5,033,463 | A | 7/1991 | Cocozza |
| 5,035,237 | A | 7/1991 | Newell et al. |
| 5,042,472 | A | 8/1991 | Bunin |
| 5,161,524 | A | 11/1992 | Evans |
| 5,186,164 | A | 2/1993 | Raghuprasad |
| 5,201,308 | A | 4/1993 | Newhouse |
| 5,239,991 | A | 8/1993 | Chawla et al. |
| 5,239,992 | A | 8/1993 | Bougamont et al. |
| 5,239,993 | A | 8/1993 | Evans |
| 5,327,883 | A | 7/1994 | Williams et al. |
| 5,347,999 | A | 9/1994 | Poss et al. |
| 5,349,947 | A | 9/1994 | Newhouse et al. |
| 5,372,128 | A * | 12/1994 | Haber et al. ............ 128/203.21 |
| 5,388,572 | A | 2/1995 | Mulhauser et al. |
| 5,394,868 | A | 3/1995 | Ambrosio et al. |
| 5,408,994 | A | 4/1995 | Wass et al. |
| 5,415,162 | A | 5/1995 | Casper et al. |
| 5,429,122 | A | 7/1995 | Zanen et al. |
| 5,437,270 | A | 8/1995 | Braithwaite |
| 5,437,271 | A | 8/1995 | Hodson et al. |
| 5,469,843 | A | 11/1995 | Hodson |
| 5,476,093 | A | 12/1995 | Lankinen |
| 5,503,144 | A | 4/1996 | Bacon |
| 5,505,196 | A | 4/1996 | Herold et al. |
| 5,522,383 | A | 6/1996 | Calvert et al. |
| 5,533,502 | A | 7/1996 | Piper |
| 5,546,932 | A | 8/1996 | Galli |
| 5,575,280 | A | 11/1996 | Gupte et al. |
| 5,590,645 | A | 1/1997 | Davies et al. |
| 5,595,175 | A | 1/1997 | Malcher et al. |
| 5,615,670 | A | 4/1997 | Rhodes |
| 5,619,984 | A | 4/1997 | Hodson et al. |
| 5,628,307 | A | 5/1997 | Clark et al. |
| 5,642,727 | A * | 7/1997 | Datta et al. ............ 128/203.15 |
| 5,651,359 | A | 7/1997 | Bougamont et al. |
| 5,653,227 | A | 8/1997 | Barnes et al. |
| 5,655,523 | A | 8/1997 | Hodson et al. |
| 5,657,749 | A | 8/1997 | Cox |
| 5,669,378 | A | 9/1997 | Pera et al. |
| 5,673,685 | A | 10/1997 | Heide et al. |
| 5,673,686 | A | 10/1997 | Villax et al. |
| 5,692,496 | A | 12/1997 | Casper et al. |
| 5,694,920 | A | 12/1997 | Abrams et al. |
| 5,699,789 | A | 12/1997 | Hendricks |
| 5,724,959 | A | 3/1998 | McAughey et al. |
| 5,740,793 | A | 4/1998 | Hodson et al. |
| 5,743,250 | A | 4/1998 | Gonda et al. |
| 5,752,505 | A | 5/1998 | Ohki et al. |
| 5,775,320 | A | 7/1998 | Patton et al. |
| 5,787,881 | A | 8/1998 | Chawla |
| 5,829,434 | A | 11/1998 | Ambrosio et al. |
| 5,857,456 | A | 1/1999 | Sun et al. |
| 5,860,419 | A | 1/1999 | Davies et al. |
| 5,875,776 | A | 3/1999 | Vaghefi |
| 5,881,719 | A | 3/1999 | Gottenauer et al. |
| 6,026,809 | A | 2/2000 | Abrams et al. |
| 6,029,663 | A | 2/2000 | Eisele et al. |
| 6,065,472 | A | 5/2000 | Anderson et al. |
| 6,071,498 | A | 6/2000 | Narodylo et al. |
| 6,089,227 | A | 7/2000 | Nilsson |
| 6,098,619 | A | 8/2000 | Britto et al. |
| 6,138,673 | A | 10/2000 | Shepherd |
| 6,152,130 | A | 11/2000 | Abrams et al. |
| 6,182,655 | B1 | 2/2001 | Keller et al. |
| 6,230,707 | B1 | 5/2001 | Hörlin |
| 6,234,169 | B1 | 5/2001 | Bulbrook et al. |
| 6,237,590 | B1 | 5/2001 | Leedom et al. |
| 6,237,591 | B1 | 5/2001 | Jackson |
| 6,257,233 | B1 | 7/2001 | Burr et al. |
| 6,286,507 | B1 | 9/2001 | Jahnsson |
| 6,328,033 | B1 | 12/2001 | Avrahami |
| 6,378,519 | B1 | 4/2002 | Davies et al. |
| 6,425,888 | B1 | 7/2002 | Embleton et al. |
| 6,427,688 | B1 | 8/2002 | Ligotke et al. |
| 6,484,718 | B1 | 11/2002 | Schaeffer et al. |
| 6,521,260 | B1 | 2/2003 | Staniforth |
| 6,561,186 | B2 | 5/2003 | Casper et al. |
| 6,626,173 | B2 | 9/2003 | Genova et al. |
| 6,651,341 | B1 | 11/2003 | Myrman et al. |
| 6,655,380 | B1 | 12/2003 | Andersson et al. |
| 6,655,381 | B2 | 12/2003 | Keane et al. |
| 6,698,425 | B1 | 3/2004 | Widerström |
| 6,715,486 | B2 | 4/2004 | Gieschen et al. |
| 6,752,147 | B1 | 6/2004 | Goldemann et al. |
| 6,779,520 | B1 | 8/2004 | Genova et al. |
| 6,780,508 | B1 | 8/2004 | Caponetti et al. |
| 6,810,872 | B1 | 11/2004 | Ohki et al. |
| 6,840,239 | B2 | 1/2005 | Myrman |
| 6,889,690 | B2 | 5/2005 | Crowder et al. |
| 6,971,383 | B2 | 12/2005 | Hickey et al. |
| 6,983,748 | B2 | 1/2006 | Brown et al. |
| 7,011,818 | B2 | 3/2006 | Staniforth |
| 7,025,056 | B2 | 4/2006 | Eason et al. |
| 7,032,593 | B2 | 4/2006 | Johnston et al. |
| 7,069,929 | B2 | 7/2006 | Young et al. |
| 7,107,988 | B2 | 9/2006 | Pinon et al. |
| 7,118,010 | B2 | 10/2006 | Crowder et al. |
| 7,143,765 | B2 * | 12/2006 | Asking et al. ............ 128/203.15 |
| 7,228,860 | B2 | 6/2007 | Andersson et al. |
| 7,252,087 | B2 | 8/2007 | Wachtel |
| 7,278,425 | B2 | 10/2007 | Edwards et al. |
| 7,284,553 | B2 | 10/2007 | Hochrainer |
| 7,401,713 | B2 | 7/2008 | Ede et al. |
| 7,556,035 | B2 | 7/2009 | Young et al. |
| 7,617,822 | B2 | 11/2009 | De Boer et al. |
| 7,718,163 | B2 | 5/2010 | Staniforth |
| 7,735,485 | B2 | 6/2010 | Yamashita et al. |

(56) References Cited

U.S. PATENT DOCUMENTS

| | | |
|---|---|---|
| 7,810,494 B2 | 10/2010 | Harmer et al. |
| 7,958,890 B2 | 6/2011 | Gieschen et al. |
| 8,037,880 B2 | 10/2011 | Zhu et al. |
| 2004/0094152 A1 | 5/2004 | Harvey et al. |
| 2004/0206773 A1 | 10/2004 | Ede et al. |
| 2004/0244794 A1 | 12/2004 | Richards |
| 2005/0172962 A1 | 8/2005 | Gumaste et al. |
| 2005/0194008 A1 | 9/2005 | Andersson et al. |
| 2005/0274378 A1* | 12/2005 | Bonney et al. ............ 128/200.23 |
| 2006/0005833 A1* | 1/2006 | Gieschen et al. ........ 128/203.15 |
| 2007/0163574 A1* | 7/2007 | Rohrschneider et al. ................ 128/200.19 |
| 2007/0209661 A1 | 9/2007 | Smyth et al. |
| 2007/0215149 A1 | 9/2007 | King et al. |
| 2008/0078689 A1 | 4/2008 | Pentafragas |
| 2008/0115785 A1* | 5/2008 | Eason et al. ............ 128/203.15 |
| 2008/0314384 A1 | 12/2008 | Harris et al. |
| 2009/0084379 A1 | 4/2009 | Goeckner et al. |
| 2009/0165790 A1 | 7/2009 | Crowder et al. |
| 2009/0178676 A1 | 7/2009 | Villax et al. |
| 2009/0235929 A1* | 9/2009 | Egen et al. ............... 128/203.15 |
| 2009/0250058 A1 | 10/2009 | Lastow et al. |
| 2009/0308392 A1 | 12/2009 | Smutney et al. |
| 2009/0320838 A1 | 12/2009 | Malhotra et al. |
| 2010/0000529 A1 | 1/2010 | Prime et al. |
| 2010/0059049 A1 | 3/2010 | Genosar |
| 2010/0300440 A1 | 12/2010 | Deboeck et al. |
| 2010/0326438 A1 | 12/2010 | Dunne |
| 2011/0120467 A1 | 5/2011 | Pardonge |
| 2012/0145150 A1 | 6/2012 | Donovan et al. |

OTHER PUBLICATIONS

Hickey, A., et al., "A New Millennium for Inhaler Technology," Pharmaceutical Technology, Jun. 1997, 7 pages.

International Search Report and Written Opinion of PCT/US2011/063816 mailed Mar. 21, 2012, 8 pages.

Martonen, T., et al., "Issues in Drug Delivery: Concepts and Practice," Respiratory Care, Sep. 2005, vol. 50, No. 9, 25 pages.

Peart, J., et al., "New Developments in Dry Powder Inhaler Technology," American Pharmaceutical Review, 2001, vol. 4, 7 pages.

Prime, D., et al., "Review of Dry Powder Inhalers," Advanced Drug Delivery Reviews, 1997, vol. 26, 8 pages.

Smyth, H., et al., "Carriers in Drug Powder Delivery—Implications for Inhalation System Design," American Journal of Drug Delivery, 2005, vol. 3, Iss. 2, 17 pages.

* cited by examiner

SECTION A-A

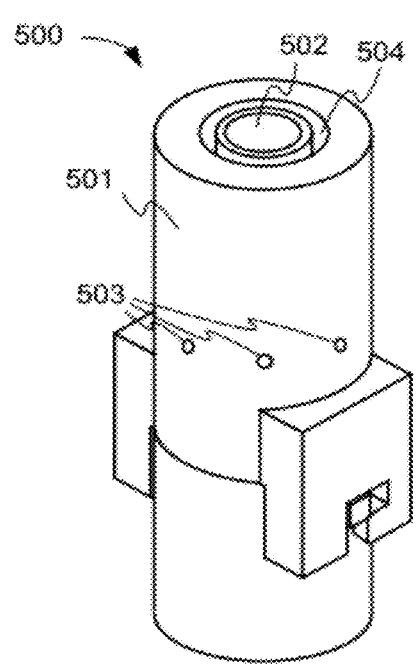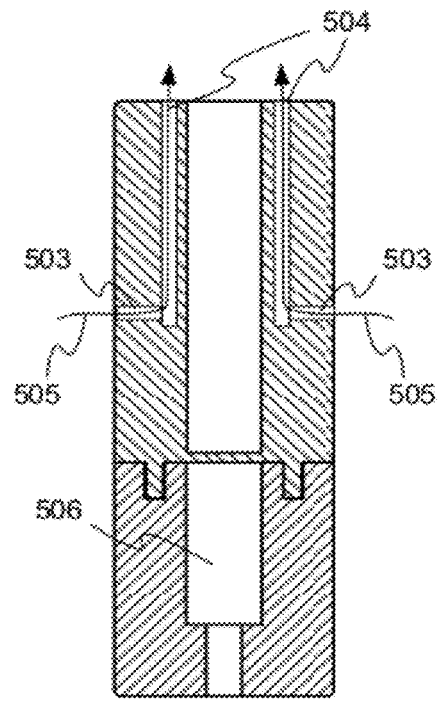
FIG. 5A  FIG. 5B
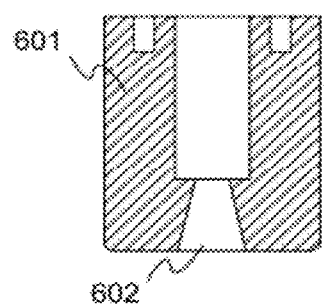
FIG. 6

BEAD-CONTAINING DRY POWDER INHALER

CROSS-REFERENCES TO RELATED APPLICATIONS

This application is a continuation-in-part of U.S. patent application Ser. No. 13/313,778 filed Dec. 11, 2011 and titled "Bead-Containing Dry Power Inhaler" which claims priority to U.S. Provisional Application No. 61/420,639 filed Dec. 7, 2010 and titled "Dry Powder Inhaler" and to U.S. Provisional Application No. 61/442,872 filed Feb. 15, 2011 and titled "Dry Powder Inhaler", the entire disclosures of which are hereby incorporated by reference herein.

BACKGROUND OF THE INVENTION

The benefits of inhaled therapy for treatment of lung diseases such as asthma, chronic obstructive pulmonary disease (COPD), and cystic fibrosis have been recognized for many years. Direct administration of drug to the airways minimizes systemic side effects, provides maximum pulmonary specificity, and imparts a rapid onset of action.

Dry powder inhalers (DPIs) are becoming a leading device for delivery of therapeutics to the airways of patients. Currently, all marketed dry powder inhalation products are comprised of micronized drug (either agglomerated or blended) delivered from "passive" dry powder inhalers, DPIs. These inhalers are passive in the sense that they rely on the patient's inspiratory effort to disperse the powder into a respirable aerosol.

Despite their popularity and the pharmaceutical advantages over other inhaler types, passive dry powder inhalers typically have relatively poor performance with regard to consistency. In particular, DPIs emit different doses depending on how the patient uses the device, for example, the inhalation effort of the patient.

Also, the efficiency of DPIs can be quite poor. In one study comparing the performance of the two most widely prescribed DPIs, only between 6% and 21% of the dose emitted from the device was considered respirable. Improved performance for DPI devices is desperately needed from both clinical and product development standpoints. One promising approach to improving DPI performance is to modify the formulation rather than the device itself.

Conventional formulations for dry powder inhalation aerosols typically contain micronized drug of particle sizes small enough to enter the airways and be deposited in the lung. To make these highly cohesive and very fine particles dispersible, so called "carrier" particles are mixed with the drug particles. These coarse, and pharmaceutically inactive (or inert), carrier particles are found in nearly all dry powder inhaler products currently marketed. The carrier particles serve to increase the fluidization of the drug because the drug particles are normally too small to be influenced significantly by the airflow through the inhaler. The carrier particles thus improve the dose uniformity by acting as a diluent or bulking agent in the formulation.

Although these carrier particles, which are generally about 50-100 microns in size, improve the performance of dry powder aerosols, the performance of dry powder aerosols remains relatively poor. For instance, only approximately 30% of the drug in a typical dry powder aerosol formulation will be delivered to the target site, and often much less. Significant amounts of drug are not released from these conventional carrier particles and, due to the relatively large size of the carrier in relation to the drug, the drug is deposited in the throat and mouth of the patient where it may exert unwanted side effects.

A dry powder formulation is typically a binary mixture, consisting of micronized drug particles (aerodynamic diameter typically between 1 and 5 μm) and larger inert carrier particles (typically lactose monohydrate with 63-90 μm diameters). Drug particles experience cohesive forces with other drug particles and adhesive forces with carrier particles (predominately via van der Waals forces), and it is these interparticulate forces that must be overcome in order to effectively disperse the powder and increase lung deposition efficiency. The energy used to overcome the interparticulate forces is provided by the inspired breath of the patient as they use the inhaler. The aerodynamic forces entrain and de-aggregate the powder, though variations in the inhalation effort of the patient (e.g. such as those arising from fibrosis or obstruction of the airways) significantly affect the dispersion and deposition of the drug, producing the flow-rate dependency of the inhaler. Obviously, there is a need for improved dry powder formulations employing novel carrier particles to maximize the safety and efficacy profiles of current DPI inhalers.

The active pharmaceutical ingredient (API), also called a medicament, typically constitutes less than 5% of the formulation (% w/w), with lactose comprising the vast majority of the dose. The purpose of the carrier lactose is to prevent aggregation of the drug particles due to cohesive forces, primarily van der Waals forces arising from the instantaneous dipole moments between neighboring drug particles. Due to the small size of the drug particles these resulting cohesive forces are quite strong and not readily broken apart by the aerodynamic force provided by inhalation, producing aggregates that possess poor flow properties and end up depositing in the back of the throat. By employing a binary mixture, the drug adheres to the carriers particles instead and the larger size of the carrier particles allows them to be more easily entrained in the air stream produced when the patient inhales, carrying the API toward a mesh where the carrier particle collides; the force from the collision is often sufficient to detach the drug particles from the carrier, dispersing them in the airstream and allowing their deposition within the lung. Collisions with the inner walls of the inhaler may also be significant. However, a large fraction of API remains attached to carriers that do not collide effectively with the mesh, but instead are deflected, producing insufficient force to disperse the drug particles from its surface. API that does not dissociate from these carriers, along with drug adhered to carrier particles that slip through without any contact with the mesh, are deposited in the back of the throat via inertial impaction, often causing significant side effects in the throat.

Over the past twenty years considerable research into the optimal properties of DPI formulations has been conducted. DPI formulations have required larger inert carrier particles to be blended with the small micronized (<5 microns) drug particles to improve re-dispersion of the cohesive drug particles and reduce dosing variability. Without carrier particles, micronized drug remains aggregated and almost all is simply inhaled as far as the throat, where it is swallowed and never reaches the intended target. There have been many studies investigating these carrier particles yet modifications to their physiochemical properties (size, shape, crystallinity, surface fines, roughness, etc.) have failed to yield meaningful improvements in performance of DPIs. Moreover, these carrier particles (lactose in the US), are also responsible for batch to batch variability in DPI performance. One of the most commonly studied properties of carrier particles is carrier particle diameter. Over the course of 20 years, the general rule of thumb has been established that increasing carrier particle size leads to decreased DPI performance. FIG. 1 shows several examples from previous literature that indicated that increasing carrier particle size in DPI formulations leads to decreased performance.

Some conventional DPIs permit, and sometimes even intend, carrier particles to exit the inhaler. As a result, the carrier particles must be inert, and in the United States, the FDA restricts the carrier particle material to lactose. There is thus a need for advanced formulation technologies including alternative carrier particle materials that may be more judiciously chosen based on hygroscopic properties of the carrier (e.g., a desiccant material) and the surface interactions (e.g., acid or base character of the drug and carrier) between the carrier and the drug. As such, it may be desirable to provide a DPI that is completely void of carrier particles to allow for circumventing the FDA restriction of lactose as the carrier material.

Nasal delivery is used for treatment of a variety of illnesses such as allergic rhinitis, as well as for delivery of drugs for systemic or CNS action.

Both powder and liquid nasal delivery systems are currently on the market. The liquid delivery technologies have utilized spray pump derived technology or pressurized metered dose inhalers (pMDIs) for rapid jetting of the formulation into the nasal cavity. In general, nasal formulations are solution or suspension based requiring solvents or stabilizers. These are typically administered as sprays. Metered sprays and pump sprays have several disadvantages including:

Need for priming in order to secure "dose uniformity"
   Complicated and expensive designs, involving many device parts in different materials.
   The devices are difficult to manufacture
   Formulations are less stable
   Control over deposition site in nasal cavity is poor
   Deposition of formulation is often concentrated to certain tissues and causes irritation on these areas while not treating other locations within the nasal cavity
   Positioning of the device during use is critical and heavily dependent on patient use, therefore variability in dosing to target tissues is high DPI device technologies have been applied to nasal delivery predominantly for locally acting drugs. These formulations have notable advantages such as stability and dose delivery. These can be particularly advantageous for biological drugs and drugs requiring systemic plasma concentrations. Included in these systems are modified dry powder inhalers (developed for orally inhaled aerosol delivery) with a "nostril piece" instead of a "mouth piece". Such devices are activated by nasal inhalation. These devices have also applied known concepts from DPI technology: reservoir dry powder with dose metering mechanisms—or capsule based devices needing piercing mechanisms and special loading procedures before use and after use. These device concepts inherit the same problems experienced when using DPIs for pulmonary delivery: complicated formulation, and high airflow resistance making it difficult to achieve sufficient nasal dose delivery.

To solve these device resistance problems, insufflators that "blow" the powder formulation of the drug into the nostril have been designed. In mechanical terms these devices are "bulky" and with limited portability, and impossible to operate with discretion. In addition, they suffer from the same in-use variability and regional deposition drawbacks of spray systems.

BRIEF SUMMARY OF THE INVENTION

The present invention is directed generally to dry powder inhalation aerosols and methods of delivering drug and/or therapeutic agents to a patient. More particularly, the present invention is designed to directly apply active agents to patients utilizing a novel actuating sphere or bead-like actuator design and an accompanying inhaler to take advantage of these unique properties. In some embodiments, the present invention also takes advantage of the high performance at low flow rates of a powder dispersion system so that powders can be successfully delivered to different regions of the nasal cavity.

According to one aspect, a dry powder inhaler includes an inlet channel through which air enters the inhaler, and a chamber that receives air from the inlet channel, the chamber being of a size and shape to contain a bead-like actuator to which a powdered medicament is adhered. The dry powder inhaler may optionally include a retaining member disposed at an end of the chamber opposite the inlet channel, the retaining member having one or more openings sized to permit air and the powdered medicament to pass through the retaining member, and to prevent the bead-like actuator from passing through the retaining member. An outlet channel is provided through which air and the powdered medicament leave the inhaler to be delivered to a patient. The geometry of the inhaler is such that a flow profile is generated within the chamber that causes the bead-like actuator to oscillate, thus detaching the powdered medicament from the surface of the bead-like actuator to be entrained by the air and delivered to the patient through the outlet channel. In some embodiments, the cross sectional area of the flow path through the inhaler undergoes a step increase at the entrance to the chamber. At the entrance to the chamber, the diameter of the chamber may be at least 1.5 times the diameter of the inlet channel. The inlet channel may comprise a tapered tube. The outlet channel may comprise a tube whose cross section changes along the length of the tube. In some embodiments, the outlet channel is comprised in a mouthpiece adapted to be placed within the mouth of the patient. In some embodiments, the outlet channel is comprised in a nasal adapter adapted to conform to the nostrils of the patient.

The dry powder inhaler may further comprise one or more bypass channels that receive supplemental air from outside the inhaler and deliver the supplemental air to the patient without the supplemental air having passed through the chamber. In some embodiments, the inlet channel is a first inlet channel and the chamber is a first chamber, the dry powder inhaler further comprises a second inlet channel and a second chamber. In some embodiments, air and powdered medicament leaving the first and second chambers are delivered to the outlet channel. In some embodiments, the outlet channel is a first outlet channel, the dry powder inhaler further comprises a second outlet channel, and air and powdered medicament leaving the first chamber are delivered to the first outlet channel, and air and powdered medicament leaving the second chamber are delivered to the second outlet channel. The first and second chambers may be of the same dimensions. The dry powder inhaler may be separable to permit insertion of a capsule into the chamber, the capsule containing the actuator. The dry powder inhaler may further include features for puncturing seals at ends of the capsule. Airflow through the inhaler may be driven by inspiratory effort of the patient.

In some embodiments, the dry powder inhaler is combined with the bead-like actuator. The bead-like actuator may be made of expanded polystyrene or polyolefin. The bead-like actuator may have a density between 0.001 and 5.0 g/cm³. The actuator may have a diameter of at least 500 microns, and in some cases may have a diameter in the range from between about 1000 and about 25,000 microns. In some embodiments, a combination of medicaments is adhered to the bead-like actuator so that multiple medicaments may be delivered to the patient at the same time. In some embodiments, the dry powder inhaler includes a plurality of chambers disposed on a rotary element for selectively aligning any of the chambers with the outlet channel.

According to another aspect, a method utilizes a dry power inhaler that includes an inlet channel, a chamber, and an outlet channel, the chamber holding a bead-like actuator, wherein one or more powdered medicaments are adhered to an outside surface of the bead-like actuator. A user inhales through the outlet channel, causing air to flow into the inlet channel, through the chamber, and through the outlet chamber, the flowing air also causing the bead-like actuator to oscillate to dislodge powdered medicament from the surface of the bead-like actuator to be entrained in the flowing air and carried through the outlet channel. In some embodiments, the method further includes separating or opening portions of the inhaler comprising the chamber and the outlet channel, loading the bead-like actuator into the chamber, and re-engaging the two portions of the inhaler. A combination of powdered medicaments may be adhered to the bead-like actuator. In some embodiments, the dry powder inhaler includes at least two chambers, with each chamber holding at least one bead-like actuator having medicament adhered to the bead-like actuator. In this way, the flowing air causes each bead-like actuator to oscillate to dislodge powdered medicament to be inhaled. Each bead-like actuator may have the same medicament thereon. Or, in some embodiments, some of the bead-like actuators may have different medicaments thereon, e.g., the bead-like actuator in one chamber has a first medicament and the bead-like material in a second chamber has a second medicament. Further, in some cases, one or more of the bead-like actuators themselves could have multiple medicaments included thereon, e.g., the bead-like actuator in one chamber includes two or more medicaments thereon. In this way, multiple combinations of drugs may be supplied to the user.

BRIEF DESCRIPTION OF THE DRAWINGS

FIG. 1 shows several examples from previous literature indicating the relationship of carrier particle size in DPI formulations to DPI performance.

FIGS. 2A-2C illustrate certain principles utilized by embodiments of the invention.

FIG. 3 illustrates relative adhesion and detachment forces as a function of carrier size.

FIG. 4A shows an oblique view of a dry powder inhaler (DPI), according to an embodiment of the invention.

FIG. 4B shows a side view of the DPI of FIG. 4A.

FIG. 4C shows a section view of the DPI of FIG. 4A.

FIG. 4D illustrates the DPI of FIG. 4A in operation.

FIG. 5A shows an oblique view of a DPI according to another embodiment.

FIG. 5B is a cross section view of the DPI of FIG. 5A.

FIG. 6 illustrates a cross section of an alternative chamber portion, according to embodiments of the invention.

FIG. 7 illustrates a cross section view of a DPI according to another embodiment.

FIG. 8A illustrates an oblique view of a chamber portion in accordance with another embodiment.

FIG. 8B shows a cross section view of the chamber portion of FIG. 8A.

FIGS. 8C and 8D illustrate two alternative arrangements for connecting the multiple chambers to one or more outlet flow channels, according to embodiments of the invention.

FIG. 9A illustrates an oblique view of a chamber portion in accordance with another embodiment.

FIG. 9B shows a cross section view of the chamber portion of FIG. 9A.

FIG. 9C shows a cross section view of a DPI using the chamber portion of FIG. 9A, according to an embodiment of the invention.

FIG. 10 illustrates a cartridge, in accordance with an embodiment.

FIG. 11 illustrates steps in one method of producing the cartridge of FIG. 10, in accordance with an embodiment.

FIG. 12 illustrates additional steps in a method of producing the cartridge of FIG. 10, in accordance with an embodiment.

FIG. 13 illustrates a multi-dose inhaler according to an embodiment of the invention.

FIG. 14 illustrates the multi-dose inhaler of FIG. 13, after loading.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

To facilitate the understanding of this invention, a number of terms are defined below. Terms defined herein have meanings as commonly understood by a person of ordinary skill in the areas relevant to the present invention. Terms such as “a”, “an” and “the” are not intended to refer to only a singular entity, but include the general class of which a specific example may be used for illustration. The terminology herein is used to describe specific embodiments of the invention, but their usage does not delimit the invention, except as outlined in the claims.

The use of the word “a” or “an” when used in conjunction with the term “comprising” in the claims and/or the specification may mean “one,” but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

In the description which follows like parts may be marked throughout the specification and drawing with the same reference numerals, respectively. The drawing figures are not necessarily to scale and certain features may be shown exaggerated in scale or in somewhat generalized or schematic form in the interest of clarity and conciseness.

The various inhalers of the invention may use one or more discrete substrates onto which a substance with an active ingredient, i.e., a drug or medicament, is removably or releasably held. This substrate may be in the form of a bead-like actuator, meaning that it is a discrete object, typically in the shape of a sphere or a shape approximating a sphere, and having an outer surface to which the substance is removably or releasably held. The substrate has the ability to move back and forth, e.g., oscillate, within a flow path created within the inhaler in order to dislodge the medicament where the substance can exit the inhaler and enter the patient's lungs. This flow path may be in the form of air or other respiratory gases flowing through the inhaler along a variety of trajectories, typically in response to a breathing maneuver from the patient or other external means to produce the flows. However, as described herein, other techniques may be used to oscillate the bead-like actuator. This bead-like actuator may also be referred herein to an actuator, an actuating sphere, a sphere, or simply a bead. In some cases, the bead-like actuator is a large bead (typically spherical or near spherical in geometry) or other bearing-type object comprised of a low-density, mechanically elastic material, which is prepared using any suitable technique, for example injection molding, compression molding, or cast material over a core. The bead-like actuator or actuating sphere may be made from ionomeric resins, polyurethanes, silicon, and other materials. The bead-like actuator or actuating sphere, while having a generally spherical outer surface, may have a plurality of dimples or other indentations or protrusions for optimized aerodynamic properties as well as for improved retention of active agents. The actuating sphere is utilized in the context of providing a medium for attachment of active agents, thus releasing the active agent upon the introduction of force or inertia. While a spherical or near spherical shape is preferred in some embodiments, it will be appreciated that in other embodiments, the substrates (including bead-like members, actuators, and the like) may not be spherical and that other shapes could be used, as long as the substrate may experience a back and forth trajectory as air or other gases flow within the chamber to cause the medicament to dislodge from the substrate. Hence, the term bead-like may not in all embodiments imply a spherical object.

Another feature of the substrates of the invention is that they may move generally unrestricted within a chamber of the inhaler so as to dislodge any medicaments as described herein. In other words, the substrates are not constrained or anchored to the walls of the chamber. Thus, the substrates can oscillate "unanchored" within the chamber without any tension applied by some form of attachment or tether.

Active pharmaceuticals ingredients (APIs), or active agents, that may be included on any of the substrates or bead-like actuators described herein may include analgesic anti-inflammatory agents such as, acetaminophen, aspirin, salicylic acid, methyl salicylate, choline salicylate, glycol salicylate, 1-menthol, camphor, mefenamic acid, fluphenamic acid, indomethacin, diclofenac, alclofenac, ibuprofen, ketoprofen, naproxene, pranoprofen, fenoprofen, sulindac, fenbufen, clidanac, flurbiprofen, indoprofen, protizidic acid, fentiazac, tolmetin, tiaprofenic acid, bendazac, bufexamac, piroxicam, phenylbutazone, oxyphenbutazone, clofezone, pentazocine, mepirizole, and the like.

Drugs having an action on the central nervous system, for example sedatives, hypnotics, antianxiety agents, analgesics and anesthetics, such as, chloral, buprenorphine, naloxone, haloperidol, fluphenazine, pentobarbital, phenobarbital, secobarbital, amobarbital, cydobarbital, codeine, lidocaine, tetracaine, dyclonine, dibucaine, cocaine, procaine, mepivacaine, bupivacaine, etidocaine, prilocaine, benzocaine, fentanyl, nicotine, and the like. Local anesthetics such as, benzocaine, procaine, dibucaine, lidocaine, and the like.

Antihistaminics or antiallergic agents such as, diphenhydramine, dimenhydrinate, perphenazine, triprolidine, pyrilamine, chlorcyclizine, promethazine, carbinoxamine, tripelennamine, brompheniramine, hydroxyzine, cyclizine, meclizine, clorprenaline, terfenadine, chlorpheniramine, and the like. Anti-allergenics such as, antazoline, methapyrilene, chlorpheniramine, pyrilamine, pheniramine, and the like. Decongestants such as, phenylephrine, ephedrine, naphazoline, tetrahydrozoline, and the like.

Antipyretics such as, aspirin, salicylamide, non-steroidal anti-inflammatory agents, and the like. Antimigrane agents such as, dihydroergotamine, pizotyline, and the like. Acetonide anti-inflammatory agents, such as hydrocortisone, cortisone, dexamethasone, fluocinolone, triamcinolone, medrysone, prednisolone, flurandrenolide, prednisone, halcinonide, methylprednisolone, fludrocortisone, corticosterone, paramethasone, betamethasone, ibuprophen, naproxen, fenoprofen, fenbufen, flurbiprofen, indoprofen, ketoprofen, suprofen, indomethacin, piroxicam, aspirin, salicylic acid, diflunisal, methyl salicylate, phenylbutazone, sulindac, mefenamic acid, meclofenamate sodium, tolmetin, and the like. Muscle relaxants such as, tolperisone, baclofen, dantrolene sodium, cyclobenzaprine.

Steroids such as, androgenic steroids, such as, testosterone, methyltestosterone, fluoxymesterone, estrogens such as, conjugated estrogens, esterified estrogens, estropipate, 17-β estradiol, 17-β estradiol valerate, equilin, mestranol, estrone, estriol, 17β ethinyl estradiol, diethylstilbestrol, progestational agents, such as, progesterone, 19-norprogesterone, norethindrone, norethindrone acetate, melengestrol, chlormadinone, ethisterone, medroxyprogesterone acetate, hydroxyprogesterone caproate, ethynodiol diacetate, norethynodrel, 17-α hydroxyprogesterone, dydrogesterone, dimethisterone, ethinylestrenol, norgestrel, demegestone, promegestone, megestrol acetate, and the like.

Respiratory agents such as, theophilline and β2-adrenergic agonists, such as, albuterol, terbutaline, metaproterenol, ritodrine, carbuterol, fenoterol, quinterenol, rimiterol, solmefamol, soterenol, tetroquinol, tacrolimus and the like. Sympathomimetics such as, dopamine, norepinephrine, phenylpropanolamine, phenylephrine, pseudoephedrine, amphetamine, propylhexedrine, arecoline, and the like.

Antimicrobial agents including antibacterial agents, antifungal agents, antimycotic agents and antiviral agents; tetracyclines such as, oxytetracycline, penicillins, such as, ampicillin, cephalosporins such as, cefalotin, aminoglycosides, such as, kanamycin, macrolides such as, erythromycin, chloramphenicol, iodides, nitrofrantoin, nystatin, amphotericin, fradiomycin, sulfonamides, purrolnitrin, clotrimazole, itraconazole, miconazole chloramphenicol, sulfacetamide, sulfamethazine, sulfadiazine, sulfamerazine, sulfamethizole and sulfisoxazole; antivirals, including idoxuridine; clarithromycin; and other anti-infectives including nitrofurazone, and the like.

Antihypertensive agents such as, clonidine, α-methyldopa, reserpine, syrosingopine, rescinnamine, cinnarizine, hydrazine, prazosin, and the like. Antihypertensive diuretics such as, chlorothiazide, hydrochlorothrazide, bendoflumethazide, trichlormethiazide, furosemide, tripamide, methylclothiazide, penfluzide, hydrothiazide, spironolactone, metolazone, and the like. Cardiotonics such as, digitalis, ubidecarenone, dopamine, and the like. Coronary vasodilators such as, organic nitrates such as, nitroglycerine, isosorbitol dinitrate, erythritol tetranitrate, and pentaerythritol tetranitrate, dipyridamole, dilazep, trapidil, trimetazidine, and the like. Vasoconstrictors such as, dihydroergotamine, dihydroergotoxine, and the like. β-blockers or antiarrhythmic agents such as, timolol pindolol, propranolol, and the like. Humoral agents such as, the prostaglandins, natural and synthetic, for example PGE1, PGE2α, and PGF2α, and the PGE1 analog misoprostol. Antispasmodics such as, atropine, methantheline, papaverine, cinnamedrine, methscopolamine, and the like.

Calcium antagonists and other circulatory organ agents, such as, aptopril, diltiazem, nifedipine, nicardipine, verapamil, bencyclane, ifenprodil tartarate, molsidomine, clonidine, prazosin, and the like. Anti-convulsants such as, nitrazepam, meprobamate, phenytoin, and the like. Agents for dizziness such as, isoprenaline, betahistine, scopolamine, and the like. Tranquilizers such as, reserprine, chlorpromazine, and antianxiety benzodiazepines such as, alprazolam, chlordiazepoxide, clorazeptate, halazepam, oxazepam, prazepam, clonazepam, flurazepam, triazolam, lorazepam, diazepam, and the like.

Antipsychotics such as, phenothiazines including thiopropazate, chlorpromazine, triflupromazine, mesoridazine, piperracetazine, thioridazine, acetophenazine, fluphenazine, perphenazine, trifluoperazine, and other major tranquilizers such as, chlorprathixene, thiothixene, haloperidol, bromperidol, loxapine, and molindone, as well as, those agents used at lower doses in the treatment of nausea, vomiting, and the like.

Drugs for Parkinson's disease, spasticity, and acute muscle spasms such as levodopa, carbidopa, amantadine, apomorphine, bromocriptine, selegiline (deprenyl), trihexyphenidyl hydrochloride, benztropine mesylate, procyclidine hydrochloride, baclofen, diazepam, dantrolene, and the like. Respiratory agents such as, codeine, ephedrine, isoproterenol, dextromethorphan, orciprenaline, ipratropium bromide, cromglycic acid, and the like. Non-steroidal hormones or antihormones such as, corticotropin, oxytocin, vasopressin, salivary hormone, thyroid hormone, adrenal hormone, kallikrein, insulin, oxendolone, and the like.

Vitamins such as, vitamins A, B, C, D, E and K and derivatives thereof, calciferols, mecobalamin, and the like for use dermatologically. Enzymes such as, lysozyme, urokinaze, and the like. Herb medicines or crude extracts such as, Aloe vera, and the like.

Antitumor agents such as, 5-fluorouracil and derivatives thereof, krestin, picibanil, ancitabine, cytarabine, and the like. Anti-estrogen or anti-hormone agents such as, tamoxifen or human chorionic gonadotropin, and the like. Miotics such as pilocarpine, and the like.

Cholinergic agonists such as, choline, acetylcholine, methacholine, carbachol, bethanechol, pilocarpine, muscarine, arecoline, and the like. Antimuscarinic or muscarinic cholinergic blocking agents such as, atropine, scopolamine, homatropine, methscopolamine, homatropine methylbromide, methantheline, cyclopentolate, tropicamide, propantheline, anisotropine, dicyclomine, eucatropine, and the like.

Mydriatics such as, atropine, cyclopentolate, homatropine, scopolamine, tropicamide, eucatropine, hydroxyamphetamine, and the like. Psychic energizers such as 3-(2-aminopropy)indole, 3-(2-aminobutyl)indole, and the like.

Antidepressant drugs such as, isocarboxazid, phenelzine, tranylcypromine, imipramine, amitriptyline, trimipramine, doxepin, desipramine, nortriptyline, protriptyline, amoxapine, maprotiline, trazodone, and the like.

Anti-diabetics such as, insulin, and anticancer drugs such as, tamoxifen, methotrexate, and the like.

Anorectic drugs such as, dextroamphetamine, methamphetamine, phenylpropanolamine, fenfluramine, diethylpropion, mazindol, phentermine, and the like.

Anti-malarials such as, the 4-aminoquinolines, alphaaminoquinolines, chloroquine, pyrimethamine, and the like.

Anti-ulcerative agents such as, misoprostol, omeprazole, enprostil, and the like. Antiulcer agents such as, allantoin, aldioxa, alcloxa, N-methylscopolamine methylsuflate, and the like. Antidiabetics such as insulin, and the like.

Anti-cancer agent such as, cis-platin, actinomycin D, doxorubicin, vincristine, vinblastine, etoposide, amsacrine, mitoxantrone, tenipaside, taxol, colchicine, cyclosporin A, phenothiazines or thioxantheres, and the like.

For use with vaccines, one or more antigens, such as, natural, heat-killer, inactivated, synthetic, peptides and even T cell epitopes (e.g., GADE, DAGE, MAGE, etc.) and the like.

Example therapeutic or active agents also include drugs of molecular weight from 40 to 1,100 including the following: Hydrocodone, Lexapro, Vicodin, Effexor, Paxil, Wellbutrin, Bextra, Neurontin, Lipitor, Percocet, Oxycodone, Valium, Naproxen, Tramadol, Ambien, Oxycontin, Celebrex, Prednisone, Celexa, Ultracet, Protonix, Soma, Atenolol, Lisinopril, Lortab, Darvocet, Cipro, Levaquin, Ativan, Nexium, Cyclobenzaprine, Ultram, Alprazolam, Trazodone, Norvasc, Biaxin, Codeine, Clonazepam, Toprol, Zithromax, Diovan, Skelaxin, Klonopin, Lorazepam, Depakote, Diazepam, Albuterol, Topamax, Seroquel, Amoxicillin, Ritalin, Methadone, Augmentin, Zetia, Cephalexin, Prevacid, Flexeril, Synthroid, Promethazine, Phentermine, Metformin, Doxycycline, Aspirin, Remeron, Metoprolol, Amitriptyline, Advair, Ibuprofen, Hydrochlorothiazide, Crestor, Acetaminophen, Concerta, Clonidine, Norco, Elavil, Abilify, Risperdal, Mobic, Ranitidine, Lasix, Fluoxetine, Coumadin, Diclofenac, Hydroxyzine, Phenergan, Lamictal, Verapamil, Guaifenesin, Aciphex, Furosemide, Entex, Metronidazole, Carisoprodol, Propoxyphene, Digoxin, Zanaflex, Clindamycin, Trileptal, Buspar, Keflex, Bactrim, Dilantin, Flomax, Benicar, Baclofen, Endocet, Avelox, Lotrel, Inderal, Provigil, Zantac, Fentanyl, Premarin, Penicillin, Claritin, Reglan, Enalapril, Tricor, Methotrexate, Pravachol, Amiodarone, Zelnorm, Erythromycin, Tegretol, Omeprazole, and Meclizine.

Other active agents include those listed as BCS Class II agents.

The active agents mentioned above may be used in combination as required. Moreover, the above drugs may be used either in the free form or, if capable of forming salts, in the form of a salt with a suitable acid or base. If the drugs have a carboxyl group, their esters may be employed.

Figure 2A:
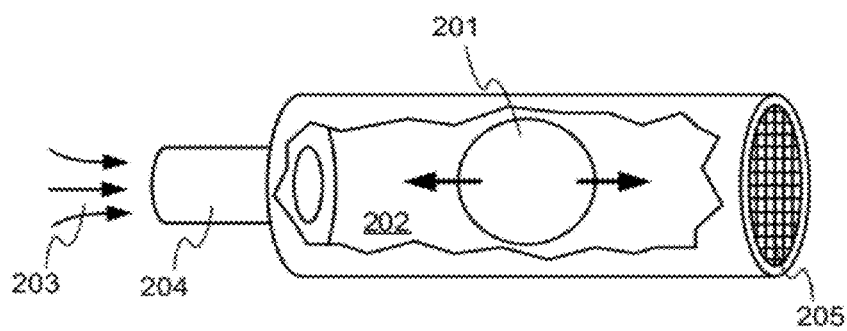
Figure 2B:
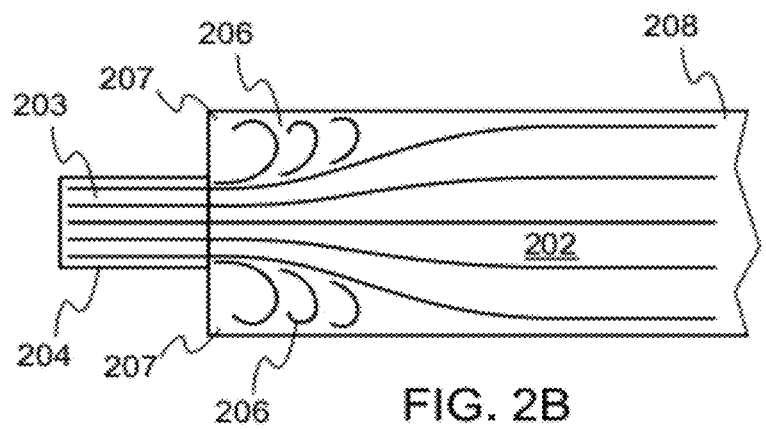
Figure 2C:
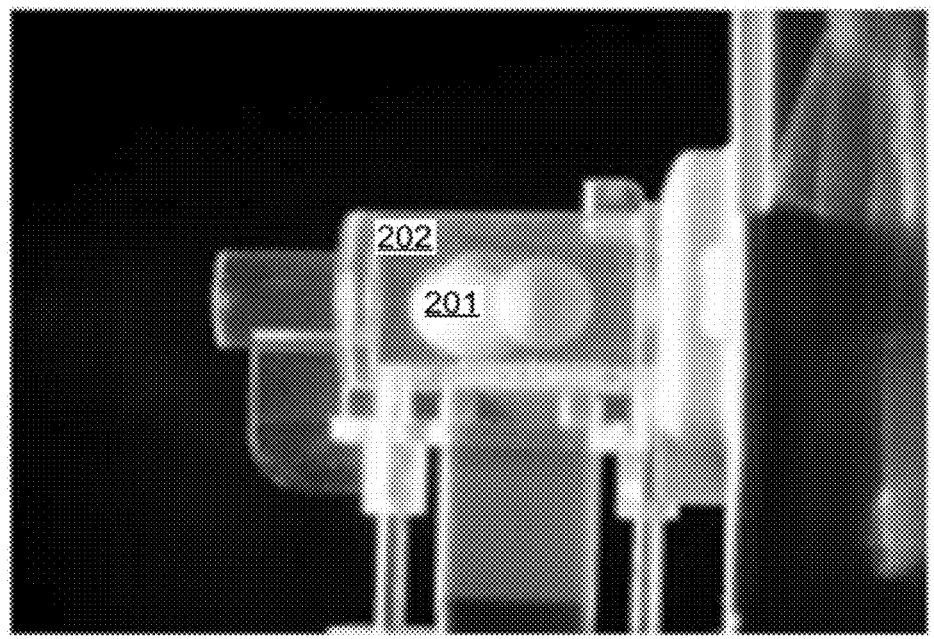

FIGS. 2A-2C illustrate certain principles utilized by embodiments of the invention. In FIG. 2A, an actuator, such as bead-like actuator 201, resides in a chamber 202. As will be explained in more detail below, a powdered medicament is adhered to actuator 201. The powdered medicament may be in a pure form, or may be adhered to carrier particles that in turn are held to actuator 201. The medicament may attach to actuator 201 by van der Waals forces, which may include combinations of permanent dipoles, induced dipoles, and instantaneous dipoles. Other attachment mechanisms may also be used, alternatively or additionally. For example, the adhesion forces may arise from van der Waals forces, electrostatic interactions, physical interactions, capillary interactions, or combinations thereof. The air 203 is drawn into chamber 202 through inlet channel 204. Inlet channel 204 is smaller in cross sectional area than the size of actuator 201, so that actuator 201 cannot enter inlet channel 204. A retaining member 205 at the other end of chamber 202 prevents actuator 201 from exiting that end of chamber 202. Retaining member 205 may be, for example, a mesh or grid that permits flow of air through the retaining member, but retains actuator 201 within chamber 202. In some embodiments, retaining member 205 may define openings that are about 250 microns in breadth, so as to prevent the passage of particles larger than about 250 microns. In other embodiments, retaining member 205 may define openings that are about 500 microns in breadth, so as to prevent the passage of particles larger than about 500 microns. Other sieve sizes are also possible. In some embodiments, retaining member 205 may have less than 50% occluded area, and in other embodiments more than 50% occluded area. When the sizes of actuator 201, chamber 202, and inlet channel 204 are properly chosen, flow of air through the system causes actuator 201 to oscillate rapidly generally in the axial direction of the flow.

The actuators, including bead-like actuators, useful in embodiments of the invention may be exemplified by actuator 201 and may be spherical or approximately spherical, but may have other shapes as well, such as, for example, elliptical, polyhedral, or other shapes. In some embodiments, the bead-like actuator may be defined in terms of a length-to-diameter ratio. As is known, the length-to-diameter ratio of a perfect sphere is 1. The bead-like actuators in certain embodiments may have a length-to-diameter ratio that is below about 2.83, and more typically in the range from about 0.25 to about 2.00. An actuator may be smooth, or have indentations, dimples, protrusions, or other surface features. An actuator may be made of any suitable material, for example a polymer such as polystyrene, polytetrafluorethylene, or another kind of polymer, polyurethane, silicon, silicone glass, silica gel, another glass, another gel, or another kind of material or combination of materials. An actuator may be made of a biodegradable material or a nonbiodegradable material. Many other kinds of materials or combinations of materials may be used. An actuator may have a relatively low density, for example, between 0.001 and 0.5 g/cm$^3$, or preferably between 0.001 and 0.12 g/cm$^3$, or more preferably between 0.02 and 0.04 g/cm$^3$. In some cases, such as when an external energy source (including a compressed gas) is used to oscillate the bead-like actuator, the density may be greater, such as, for example, up to about 5 g/cm$^3$. Even with the increased density, the bead-like actuators could be oscillated at frequencies that would induce acceptable drug detachment and performance. An actuator may be of any appropriate size compatible with the chamber in which it is retained. For example, an actuator may have a diameter or other largest dimension of between 500 and 25000 microns (0.5 and 25 mm), preferably between 1000 and 10000 microns (1.0 and 10.0 mm), and more preferably between 1000 and 6000 microns (1.0 and 6.0 mm), and still in other cases from about 3,000 to 5,500 microns. An actuator may be made by any suitable process, depending on the material of the actuator. For example, actuators may be made by molding, extrusion, milling, spray drying, polymer imprinting, or other processes or combinations of processes. In some embodiments, an actuator may have a mass of less than 10.0 mg, for example less than 5.0 mg, or less than 2.5 mg. In other embodiments, an actuator may have a mass of greater than 0.001 mg, for example greater than 0.1 mg, or greater than 0.5 mg. In some embodiments, an actuator may have a mass between 0.001 mg and 10.0 mg, for example, between 0.1 mg and 5.0 mg, or between 0.5 mg and 2.5 mg.

FIG. 2B illustrates the formation of re-circulating eddies 206 in empty chamber 202. As the flow stream enters chamber 202, the flow stream detaches from the inner wall of the system at the corner of the expansion, where inlet channel 204 opens to chamber 202, and reattaches downstream. At the corner of this expansion, part of the incoming flow stream is shed, becoming trapped as recirculating eddies 206 at the corners 207 of chamber 202. Once actuator 201 is introduced into chamber 202, the flow may become more complex. The net result is that actuator 201 oscillates rapidly, generally along the axis of chamber 202. Actuator 201 may also rotate in up to three dimensions.

FIG. 2C is a multiple-exposure photograph of an actual system, in which actuator 201 oscillates. It has been surprisingly discovered that during oscillation, actuator 201 rarely contacts the walls or ends of chamber 202. However, the oscillations of actuator 201 are sufficient in magnitude to dislodge powdered medicament from the surface of actuator 201.

Figure 3:
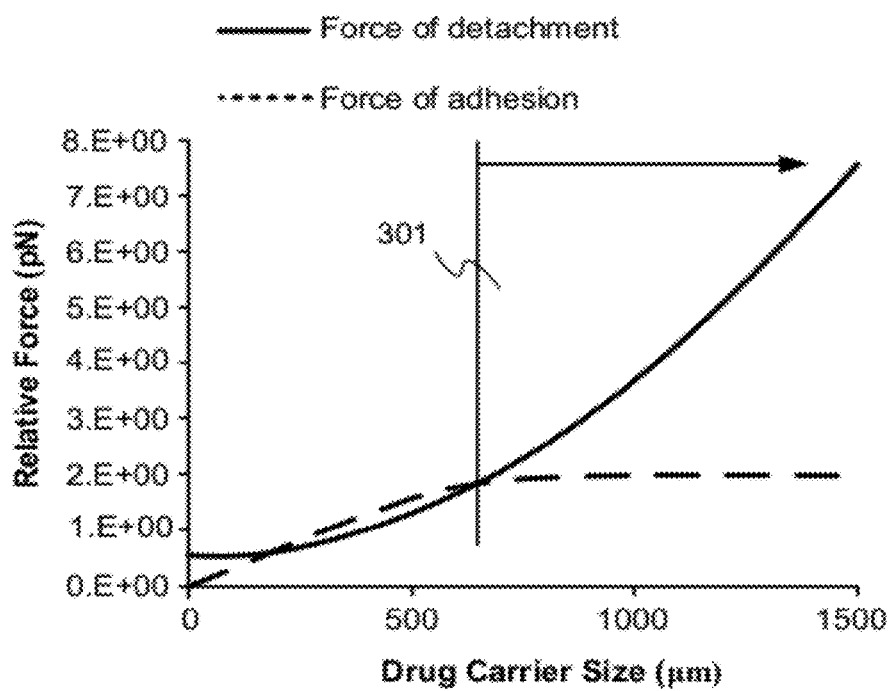

This is in part due to the relatively large size of actuator 201, as compared with carrier particles used in previous inhalers. The adhesive forces holding powdered medicament to a carrier particle may be approximated by $$F_{adhesive} = \frac{A_H d_1 d_2}{12D^2(d_1 + d_2)}$$

where $A_H$ is the Hamaker's constant, and is typically on the range of $10^{-19}$ J, D is the interparticulate distance and is commonly given as 4 Angstroms ($10^{-10}$ m), and $d_1$ and $d_2$ are the diameters of the medicament and carrier particles respectively. The separation forces generated by the oscillation of actuator 201 are generally proportional to the cube of the diameter of actuator 201. Thus, for a large actuator, it is possible to generate separation forces that exceed the adhesive forces, as shown in FIG. 3, in region 301.

According to embodiments of the invention, these principles are utilized to produce an inhaler with improved performance.

Inhaler Embodiments

Figure 4A:
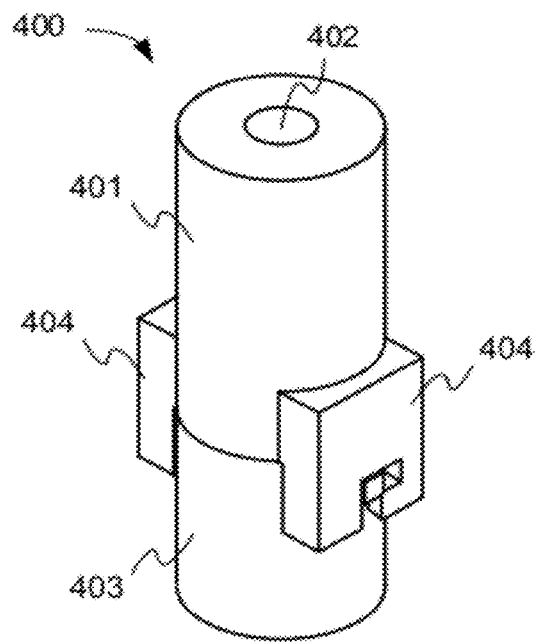
Figure 4B:
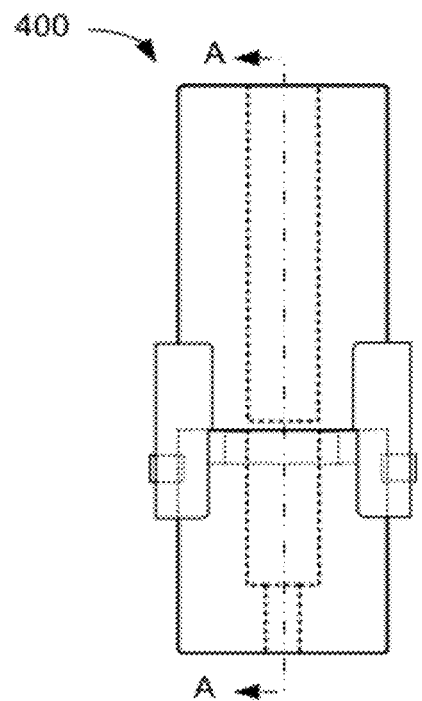
Figure 4C:
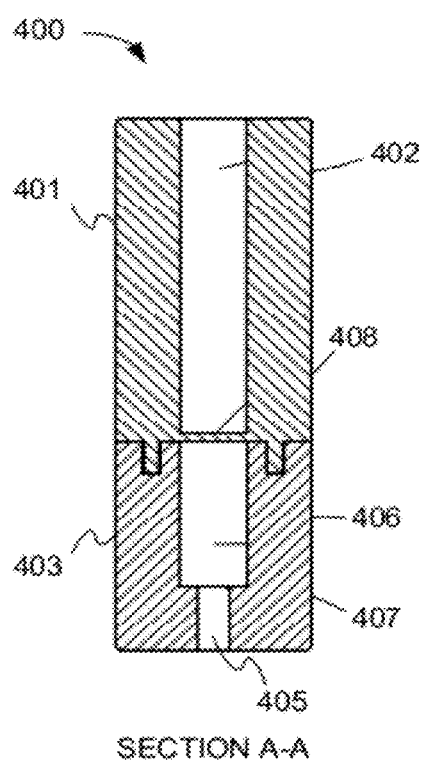

FIG. 4A shows an oblique view of a dry powder inhaler (DPI) 400, according to an embodiment of the invention. DPI 400 includes a mouthpiece 401, through which outlet channel 402 passes. DPI 400 also includes a chamber portion 403, engaged with mouthpiece 401. DPI 400 may also include retaining features 404, for holding mouthpiece 401 and chamber portion 403 together. Connection features 404 may be releasable, to allow mouthpiece 401 and chamber portion 403 to be separated and reattached, for example for loading of DPI 400. Any suitable connection mechanism may be used. FIG. 4B shows a side view of DPI 400, and FIG. 4C shows a section view of DPI 400, revealing some internal details.

Chamber portion 403 of DPI 400 includes an inlet channel 405, leading to a chamber 406. Optionally, the inside surface of chamber 406 may include ridges or other surface features to minimize the contact area of an actuator contained in chamber 406 with the walls. Chamber 406 has a larger cross sectional area than does inlet channel 405, and at the entrance 407 of chamber 406, the flow path of air through DPI 400 undergoes a step increase in cross sectional area. Chamber 406 is of a size and shape to contain an actuator to which a powdered medicament is adhered. DPI 400 also includes a retaining member 407 downstream of chamber 406. Retaining member 407 includes openings (not visible in FIG. 4C) sized to permit air to flow through retaining member 408, but to retain the actuator within chamber 406. Retaining member may be, for example, a mesh or grid placed across an end of chamber 406 or outlet channel 402.

Figure 4D:
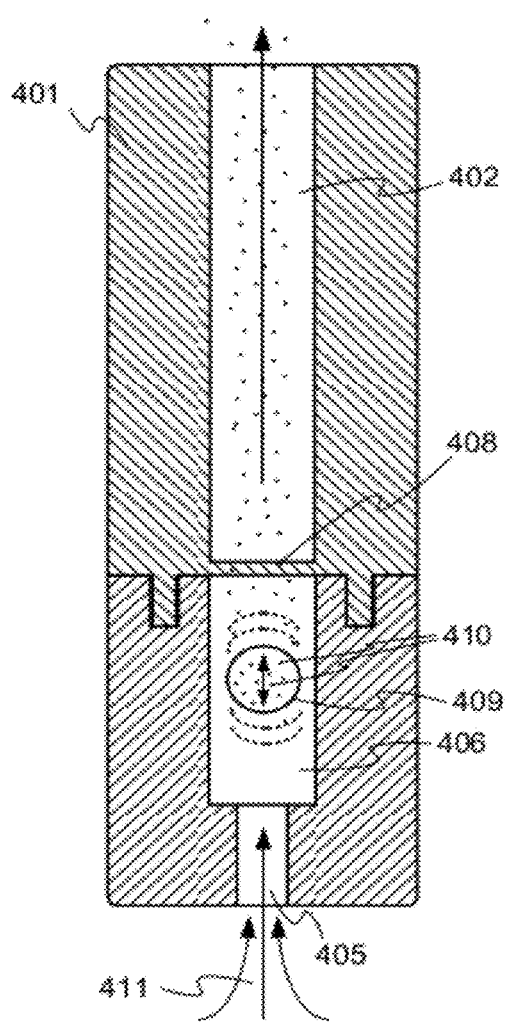

FIG. 4D illustrates DPI 400 in operation. In FIG. 4D, an actuator or bead-like actuator 409 has been loaded into chamber 406. Actuator 409 is large enough that it cannot pass through inlet channel 405 and cannot pass through the openings in retaining member 408, and thus actuator 409 is retained within chamber 406. Actuator 409 may be spherical or substantially spherical, although this is not a requirement. Because actuator 409 does not leave chamber 406 or come into contact with the patient, it need not be made of lactose, and more flexibility in the selection of materials for actuator 409 is provided than for the carrier particles in a conventional inhaler. Actuator 409 may be, for example, made of polystyrene, polytetrafluoroethylene (PTFE, aka Teflon), silicone glass, silica gel, glass, or another suitable material. In some embodiments, actuator 409 may be made of a biodegradable material.

Particles 410 of a powdered medicament (shown exaggerated in size in FIG. 4D) are adhered to actuator 409. A patient places mouthpiece 401 in his or her mouth, and inhales. The inspiratory effort of the patient draws air 411 into inlet channel 405. As previously explained, actuator 409 oscillates generally along the axial direction of the flow channel, dislodging particles 410 from the surface of actuator 409 such that they are entrained in the flow stream. The dislodged particles 410 pass through retaining member 408, through outlet channel 402, and exit DPI 400 to be inhaled by the patient. Outlet channel 402 may include ridges or grooves (similar to the rifling in the barrel of a firearm) to assist in directing the flow of the medicament in a straight path as it leaves the device. Actuator 409 may oscillate many of times during a single inhalation, and may oscillate as many as hundreds of times. The oscillation frequency is typically between 1 and 1,000 Hz, and is preferably between 25 and 150 Hz, although other frequencies may also occur. However, in some cases, the oscillation frequency could be up to about 5,000 Hz, and in other cases up to about 10,000 Hz. The oscillation may produce an audible sound, which can provide audible feedback to a patient using the DPI, indicating that medicament is being delivered. The amplitude (or maximal linear length of travel in a single direction) of the bead-like actuator's path may depend on the length of the chamber 406 and the size of the bead-like actuator, among other variables.

One important aspect is that the bead-like actuator oscillates within chamber 406 without generally contacting the ends of chamber 406. In other words, the design of the inhaler causes the bead-like actuator to change direction (as it oscillates along its full amplitude) without generally contacting the ends of the chamber. In some situations, such as during times of non-use, manufacture of the inhaler and during initial actuation, the bead-like actuator may contact the side walls and/or one of the ends of the chamber or being tethered to the chamber. Further, although the bead-like actuator may experience some incidental contact while oscillating (when the user inhales or actuates the inhaler), it will generally be able to freely move within the chamber and change directions without substantial contact with the chamber. It is this rapid change of direction of the bead-like actuator that creates the dispersive forces needed to dislodge and separate the powder from the bead-like actuator. This may be referred to as a natural oscillating frequency, i.e., the bead-like actuator travels its full amplitude before changing direction due to the flow pattern within the chamber.

These oscillations impart sufficient forces to detach the majority of the drug from the bead surface, allowing it to be entrained in the inhalation flow stream and delivered from the device.

An inhaler that is actuated by the patient's inspiratory effort alone is known as a passive inhaler. It will be recognized that the invention may be embodied in a passive inhaler, or an inhaler that uses another energy source, such as a compressed or pressurized gas, at least in part to promote air flow. As another example, oscillations of the bead-like actuator may be induced using one or more magnetic fields. For instance, the drug-coated bead-like actuator could be constructed of a metallic bead that is exposed to multiple magnetic fields that are arranged such that one (magnetic field A) will attract the bead to one end of the dispersion chamber and another (magnetic field B) will attract the bead to the opposite end of the dispersion chamber. To oscillate the bead, the bead will need to "feel" the pull from one magnetic field (e.g., magnetic field A) with greater strength than it feels the pull from the other (magnetic field B) thereby driving the bead in one direction, and then rapidly reverse the direction by increasing the pull of the other magnetic field (B) relative to magnetic field A. One method to achieve this is to employ a spinning disk that partially occludes/mitigates a magnetic field, such that this device periodically interrupts the magnetic field (similar to an optical chopper that periodically interrupts a light beam). The magnetic field, or "chopper(s)", can be induced to move either passively (inhalation flow only) or actively (external energy source), and timed such that the blocking of the magnetic field is alternated, inducing the bead to oscillate rapidly, and detaching the drug from the surface of the bead.

Other embodiments may be to include a polymeric bead with a piece of metal embedded within it, or a metallic bead with a polymeric coating onto which the drug is coated. With each of these embodiments, the bead may be induced to oscillate using alternating magnetic fields as described above.

Within this basic framework, many variations are possible. FIG. 5A shows an oblique view of a DPI 500 according to another embodiment. DPI 500 includes several features similar to features of DPI 400 previously described, including a mouthpiece 501 including an outlet flow channel 502. DPI 500 also includes flow bypass channels 503 that are connected to a sheath flow channel 504. FIG. 5B is a cross section view of DPI 500, showing the internal configuration of flow bypass channels 503 and sheath flow channel 504. Supplemental air 505 is drawn into flow bypass channels 505 and through sheath flow channel 504, reaching the patient without having passed through chamber 506. Flow bypass channels may be included to reduce the flow resistance of DPI 500, while still allowing sufficient airflow through chamber 506 to deliver powdered medicament to the patient. For example, in a direct comparison, a device without bypass flow channels was measured to have a flow resistance of about 0.140 $(cmH_2O)^{0.5}/L\ min^{-1}$, resulting in a flow rate of about 46 L $min^{-1}$ with a pressure drop of 4 kPa across the inhaler, while a device with bypass flow channels was measured to have a flow resistance of about 0.061 $(cmH_2O)^{0.5}/L\ min^{-1}$, resulting in a flow rate of about 105 L $min^{-1}$ with a pressure drop of 4 kPa across the inhaler.

In another variation, FIG. 6 illustrates a cross section of an alternative chamber portion 601. Chamber portion 601 is similar to chamber portion 403 described above, but rather than a cylindrical inlet flow channel, chamber portion 601 includes a tapered inlet flow channel 602. Many other shapes are possible.

Figure 7:
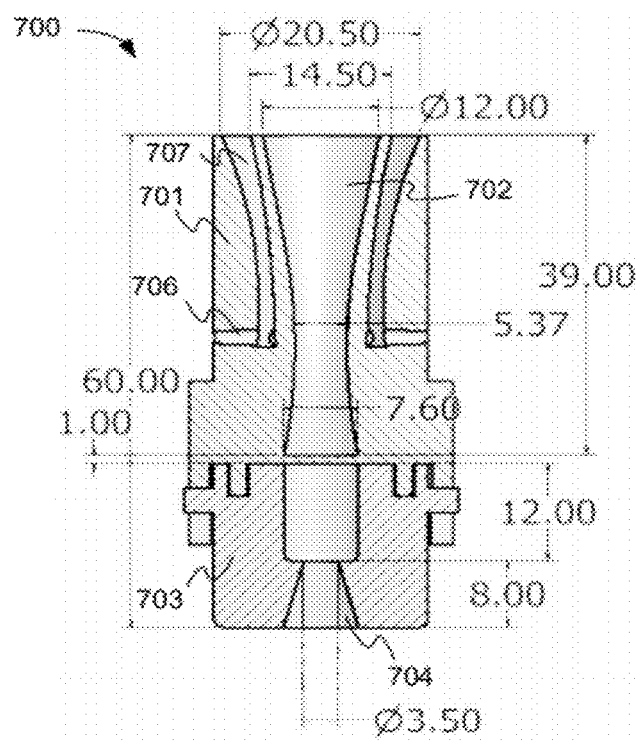

FIG. 7 illustrates a cross section view of a DPI 700 according to another embodiment, including dimensions of various features, given in millimeters. DPI 700 may accommodate an actuator having a diameter of about 4.5-5.5 millimeters, although other sizes may be used. DPI 700 includes a mouthpiece 701 having an outlet flow channel 702. Unlike outlet flow channel 402 described above, outlet flow channel 702 is not cylindrical, but changes in cross sectional area along its length. A chamber portion 703 includes an inlet flow channel 704 (which is tapered in this example), leading to a chamber 705. Bypass flow channels 706 direct supplemental air to a sheath flow channel 707 without the supplemental air having passed through chamber 705.

While DPI 700 serves as one enabling example embodiment, it will be understood that the invention claimed is not limited to the particular dimensions or combination of features shown. For example, the length of mouthpiece 701 may be shorter or longer than that shown in FIG. 7. Outlet flow channel 702 may be cylindrical or may have a cross sectional area that varies along the length of mouthpiece 701. The two ends of outlet flow channel 702 may be of equal size, or may differ in size, with either end being larger than the other. Cylindrical flow channels need not be circularly cylindrical, but may have cross sectional shapes in the form of polygons, ellipses, or other shapes. The length of inlet flow channel 704 may be varied, and inlet flow channel 704 may be cylindrical or may have a cross sectional area that varies along the length of inlet flow channel 704. Inlet flow channel 704 may be straight, tapered, curved, angled, or have another shape. Bypass flow channels 706 and sheath flow channel 707 may be varied in shape or size, or may be omitted. For example, sheath flow channel 707 may be straight, curved, tapered, angled, or may have another shape. A different number of bypass flow channels 706 may be provided. Multiple sheath flow channels 707 may be provided. The length, shape, and cross sectional area of chamber 705 may be varied from the stated dimensions, within any workable ranges.

In some embodiments, the ratio of the chamber diameter to the inlet diameter is between 1.5 and 3.0, for example between 2.10 and 2.25. In some embodiments, the ratio of the chamber diameter to the diameter of the actuator within the chamber is between 1.0 and 2.0, for example between 1.3 and 1.6.

Mouthpiece 701 and chamber portion 703 may be made of any suitable material, but preferably are molded of a medical or food grade polymer such as polycarbonate, ABS, or another polymer or blend of polymers. The parts of DPI 700 may be reusable or may be disposable.

The embodiment of FIG. 7 was measured to have a flow resistance of about 0.059 $(cmH_2O)^{0.5}/L\ min^{-1}$. Its performance was tested in vitro using a cascade impactor, at a volumetric flow rate of 90 L $min^{-1}$, which corresponds to approximately a 2 kPa pressure drop across the inhaler. Several medicaments were tested, and results are shown below in Table 1.

For the fluticasone propionate and salmeterol xinafoate drug-coated beads, coating was performed according to the piezo-assisted coating (PAC) technique. Briefly, 2 mg of micronized drug powder were weighed into a 30-mL scintillation vial containing three 5.2 mm polystyrene beads. The vial was sealed and the bottom half was submerged in a sonicating water bath for 2 minutes. When the vial was placed in the water bath, the energy imparted to the powder by the sonics aerosolized a fraction of the powder bed, creating a sustained plume as powder was continuously aerosolized and then deposited onto the bead surface by gravitational settling. Due to the small size, and thus negligible mass, of the primary drug particles, van der Waals interactions may overwhelm other types of forces, including gravitational forces. Other kinds of forces may also contribute to attachment of powder to the actuator, for example forces arising from electrostatic interactions, physical interactions, capillary interactions, or others. More information about the deposition of medicament on beads may be found in co-pending PCT Patent Application PCT/US2010/047043, published as WO/2011/031564, the entire disclosure of which is hereby incorporated by reference herein.

For fluticasone propionate and salmeterol xinafoate, drug depositing on each component of the experimental setup (bead, device, mouthpiece adaptor, USP induction port, and cascade impactor stages) was assessed via high performance liquid chromatography (HPLC). The fine particle fraction of the delivered dose was calculated as the ratio of the drug mass collected from stages 2-8 of the cascade impactor over the drug mass emitted from the device.

TABLE 1

Fine particle fractions (FPF) values of the dose delivered from the single-chamber dry powder inhaler at a volumetric flow rate of 90 L $min^{-1}$ (approx. 2 kPa pressure drop across the device).

| API | Fine Particle Fraction (%) |
|---|---|
| Salbutamol Sulphate | 84.2 (0.9) |
| Salmeterol Xinafoate | 88.5 (3.0) |
| Fluticasone Propionate | 80.5 (1.5) |
| Tiotropium Bromide | 85.2 (1.5) |

Values are presented as the mean (±standard deviation) for N = 3 replicates.

In the embodiments described thus far, a single chamber is provided, for holding a single actuator. The single actuator may have a single powdered medicament adhered to it, or may have a mixture of powdered medicaments adhered to it, so that a combination of drugs may be delivered.

In another variation, multiple chambers may be provided, for holding multiple actuators. For example, multiple actuators may have the same medicament or medicaments adhered to them, for delivering a stronger dose than is delivered from a single actuator, or may have different medicaments adhered to them for delivering a combination of drugs.

Figure 8A:
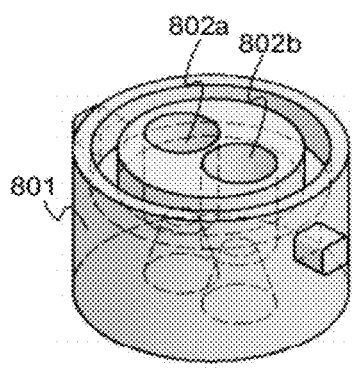
Figure 8B:
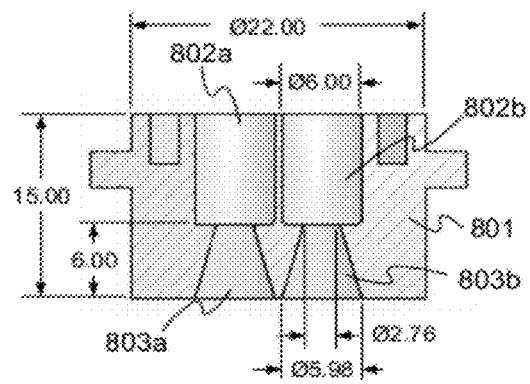

FIG. 8A illustrates an oblique view of a chamber portion 801 in accordance with another embodiment. Chamber portion 801 includes two chambers 802a and 802b, and two inlet flow channels 803a and 803b. FIG. 8B shows a cross section view of chamber portion 801, and includes example dimensions. The embodiment of FIGS. 8A and 8B may accommodate actuators having diameters between about 3.8 and 4.4 millimeters.

Figures 8C, 8D:
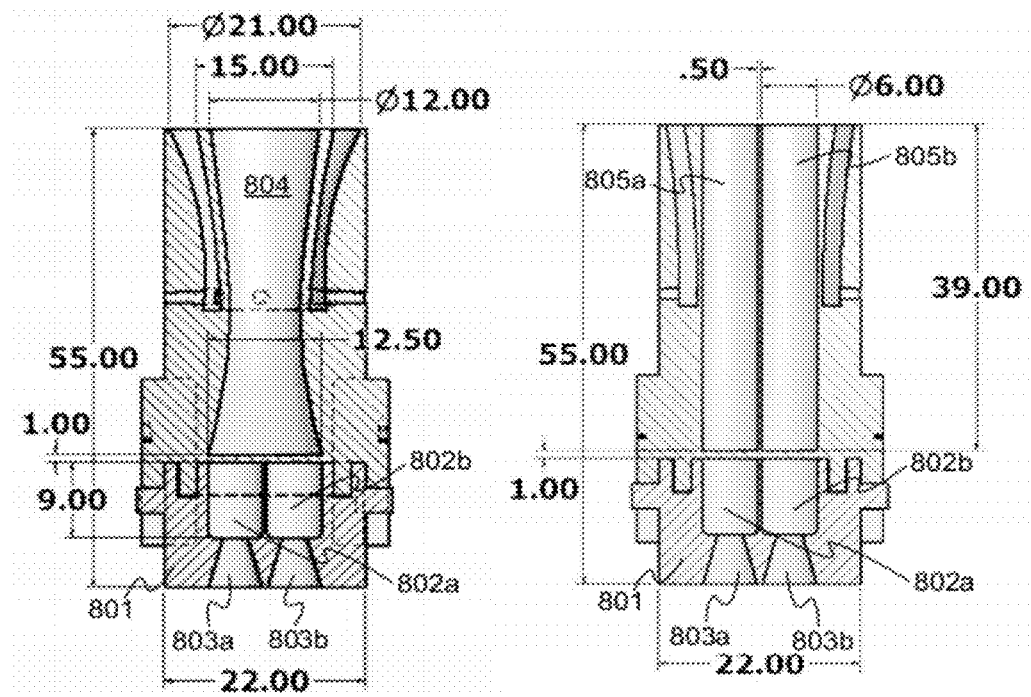

FIGS. 8C and 8D illustrate two alternative arrangements for connecting the multiple chambers 802a and 802b to one or more outlet flow channels. In the embodiment of FIG. 8C, both chambers 802a and 802b are connected to a single outlet flow channel 804. In the embodiment of FIG. 8D, chambers 802a and 802b are connected to different respective outlet flow channels 805a and 805b.

To assess the aerosol performance of the dual chamber devices (using the same inhaler base, with the type of mouthpiece being varied) in vitro, beads coated with fluticasone and salmeterol (using the PAC method) were actuated at 90 L min$^{-1}$ (corresponding to approximately a 2 kPa pressure drop across the device) into a next generation cascade impactor. Drug depositing on each component of the experimental setup (bead, device, mouthpiece adaptor, USP induction port, and cascade impactor stages) was assessed via high performance liquid chromatography (mobile phase=75:25 mixture of methanol and 0.8% (w/v) ammonium acetate buffer at a pH of 5.5; stationary phase=5 μm $C_{18}$; detection wavelength=228 nm). The fine particle fraction of the delivered dose was calculated as the ratio of the drug mass collected from stages 2-8 of the cascade impactor over the drug mass emitted from the device, corresponding to an aerodynamic diameter cut-off size of 6.48 μm (at 90 L min$^{-1}$).

The performance of the embodiment of FIG. 8C is summarized in Table 2.

TABLE 2

Fine particle fractions (FPF) values of the dose delivered from a dual-chamber dry powder inhaler at a volumetric flow rate of 90 L min$^{-1}$ (approx. 2 kPa pressure drop across the device).

| API | Fine Particle Fraction (emitted) (%) |
| --- | --- |
| Fluticasone Propionate | 76.8 (1.8) |
| Salmeterol Xinafoate | 49.1 (5.1) |

Values are presented as the mean (±standard deviation) for N = 3 replicates.

The performance of the embodiment of FIG. 8D is summarized in Table 3.

TABLE 3

Fine particle fractions (FPF) values of the dose delivered from a dual-chamber dry powder inhaler with separate powder flow channels at a volumetric flow rate of 90 L min$^{-1}$ (approx. 2 kPa pressure drop across the device).

| API | Fine Particle Fraction (emitted) (%) |
| --- | --- |
| Fluticasone Propionate | 77.5 (1.6) |
| Salmeterol Xinafoate | 54.1 (9.4) |

Values are presented as the mean (±standard deviation) for N = 3 replicates.

Figure 9A:
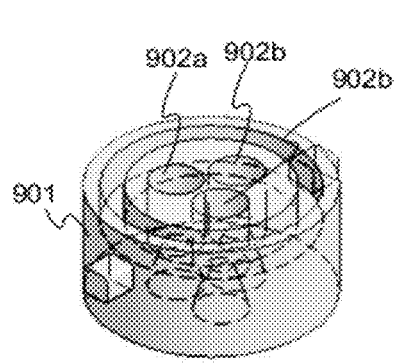
Figure 9B:
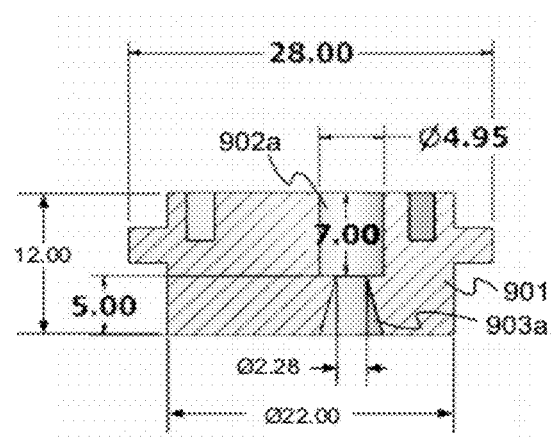

FIG. 9A illustrates an oblique view of a chamber portion 901 in accordance with another embodiment. Chamber portion 901 includes three chambers 902a, 902b, and 902c, and three inlet flow channels. FIG. 9B shows a cross section view of chamber portion 901, and includes example dimensions. Only inlet flow channel 903a is visible in FIG. 9B. The embodiment of FIGS. 9A and 9B may accommodate actuators having diameters between about 3.2 and 3.8 millimeters.

Figure 9C:
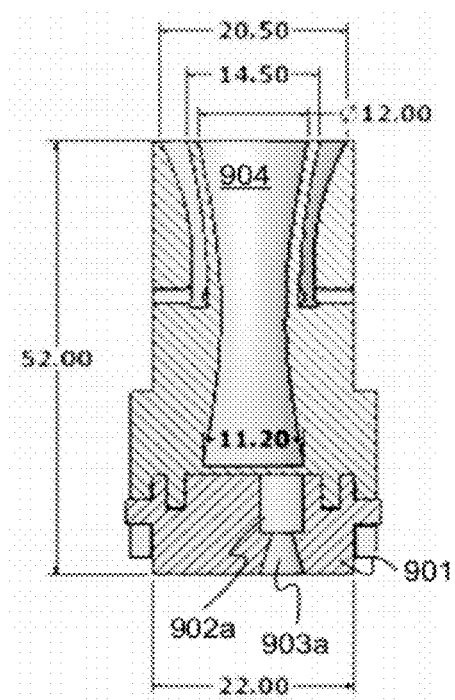

FIG. 9C illustrates the use of chamber portion 901 with a mouthpiece having a single outlet flow channel 904 to which all three of chambers 902a, 902b, and 902c deliver air and medicament. It will be understood that a mouthpiece could also be used having a separate respective outlet flow channel for each of chambers 902a, 902b, and 902c.

The examples above show dual and triple chambers, wherein the overall diameter of the inhaler has been kept constant, requiring that the dimensions of the chambers and inlet flow channels be reduced and that smaller actuators be used as compared with the single-chamber embodiments. This is not a requirement. The overall dimensions of the inhaler may be also be varied if desired.

While the embodiments of FIGS. 8A-9C serve as enabling example embodiments, it will be understood that the dimensions and combinations of features shown are by way of example, and that may variations are possible.

The embodiments described above are also configured for oral inhalation of powdered medicament. Devices embodying the invention may also be configured to deliver medicament nasally, either in place of or in addition to oral delivery. For example, the outlet flow channel or channels may be comprised in a nasal adapter.

Cartridge

According to another aspect, a cartridge is provided with a pre-loaded actuator. Such a cartridge may contain a single dose of a powdered medicament, and may be loaded into a reusable DPI that operates according to the principles of the invention.

Figure 10:
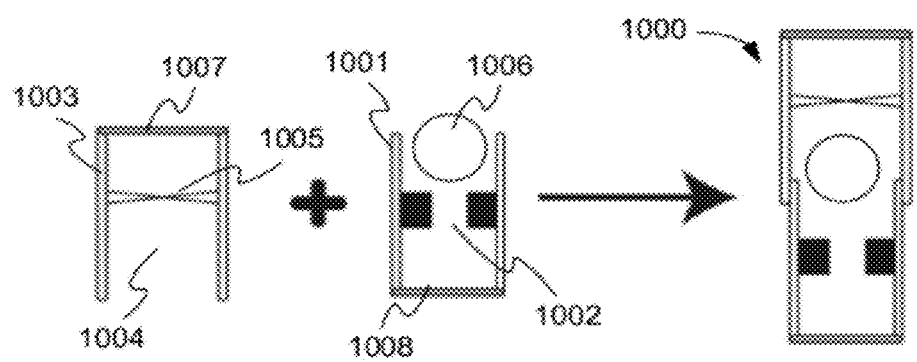

FIG. 10 illustrates a cartridge 1000, in accordance with an embodiment. Cartridge 1000 includes a first shell 1001 defining a first end of the cartridge. First shell 1001 includes a restriction 1002 that serves as an inlet flow channel. Cartridge 1000 also includes a second shell 1003 that defines a second end of the cartridge. Second shell 1003 also defines at least a portion of a chamber 1004, and includes a retaining element 1005. Retaining element 1005 may be a mesh or grid that spans the cross section of second shell 1003. An actuator 1006 is also provided, having one or more powdered medicaments adhered to it. First and second shells 1001 and 1003 are configured to engage to form the completed cartridge 1000, enclosing actuator 1006. The closed ends of first and second shells 1001 and 1003 are formed by first and second puncturable seals 1007 and 1008, which also form the ends of cartridge 1000 once first and second shells 1001 and 1003 are engaged. Each of puncturable seals 1007 and 1008 may be, for example an aluminum foil or plastic barrier that serves to keep contaminants out of cartridge 1000, but can be easily punctured (as described below) to open the ends of cartridge 1000 for use. Retaining member 1005 has openings to permit medicament dislodged from actuator 1006 to pass through retaining member 1005 during use, but retaining member does not permit actuator 1006 to leave cartridge 1000. Thus, cartridge 1000 contains and protects the actuator and medicament until it is inserted into an inhaler for use. In some embodiments, a cartridge may be used only once, to administer a single dose of medicament.

Figure 11:
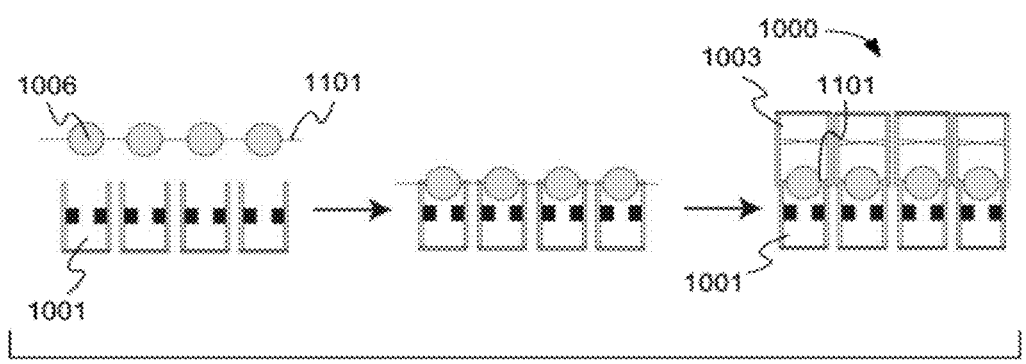

Cartridges 1000 may be produced in large numbers and distributed to inhaler users for treatment of various conditions. FIG. 11 illustrates one example method of producing cartridges 1000. A number of first shells 1001 are produced, and a number of actuators 1006 are produced and coated with medicament. Actuators 1006 are suspended on a string 1101 for convenient handling by automated production equipment. Actuators 1006 are placed into first shells 1001, and second shells 1003 are engaged with first shells 1001 to form completed cartridges 1000. In some embodiments, the action of engaging the first and second shells 1001 and 1003 cuts string 1101, so that the individual cartridges 1000 are easily separable. Preferably, a portion of string 1101 remains within each cartridge 1000, suspending actuator 1006 so that it does not readily contact the walls of the cartridge.

Figure 12:
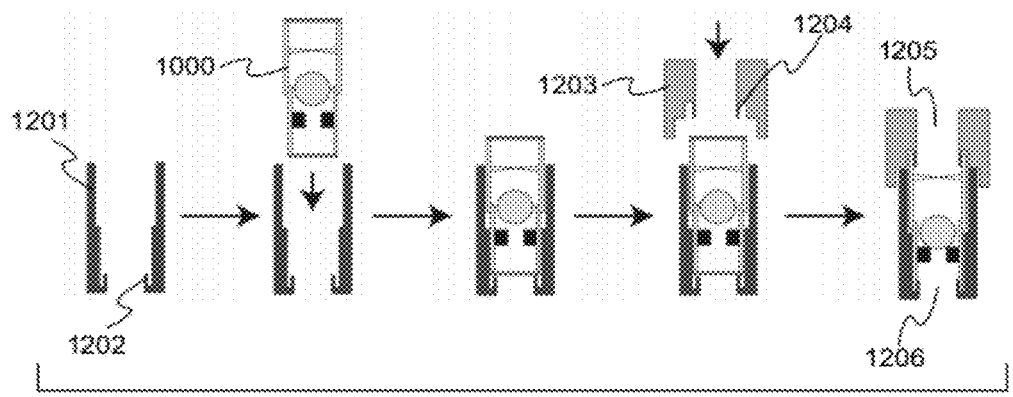

The act of loading one of cartridges 1000 into an inhaler may puncture seals 1007 and 1008, readying the cartridge for use. This process is illustrated in FIG. 12. A first portion 1201 of an inhaler is configured to receive a first end of cartridge 1000. First portion 1201 includes a lip 1202, on which cartridge 1000 rests when first loaded into first portion 1201. A second portion 1203 of the inhaler, including a second lip 1204, is then placed over cartridge 1000. When first and second portions 1201 and 1203 are pressed together, lips 1202 and 1204 puncture the seals at the ends of cartridge 1000, providing openings 1205 and 1206 for the passage of air. In some embodiments, the action of pressing first and second inhaler portions 1201 and 1203 together further compresses cartridge 1000, causing string 1101 to be cut and freeing actuator 1006 so that it can oscillate during inhalation.

Multi-Dose Dry Powder Inhaler

Figure 13:
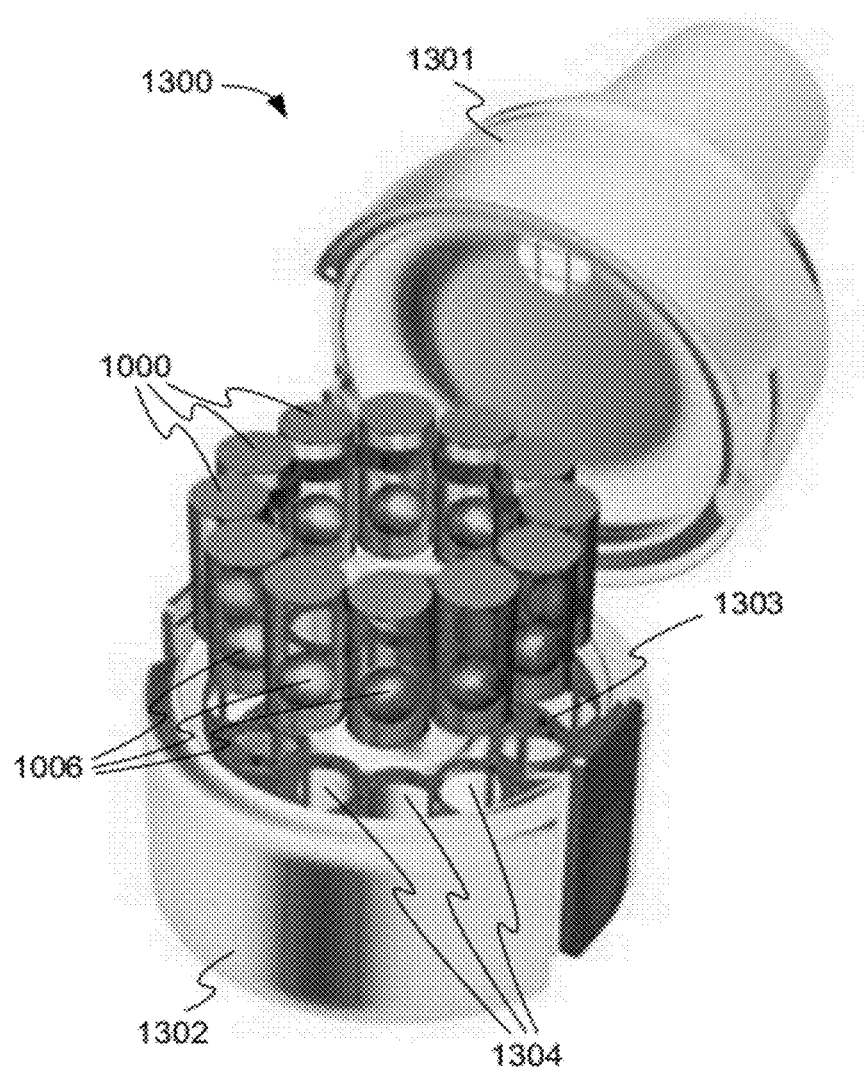

According to another aspect, a multi-dose inhaler is provided. FIG. 13 illustrates a multi-dose inhaler 1300 according to an embodiment. Multi-dose inhaler 1300 includes a mouthpiece portion 1301 and a round base portion 1302. A rotatable carriage 1303 is disposed within base portion 1302, and includes a set of slots 1304 configured to receive cartridges, for example cartridges similar to cartridge 1000 described above. Each cartridge includes an actuator 1006, on which a powdered medicament is adhered.

Figure 14:
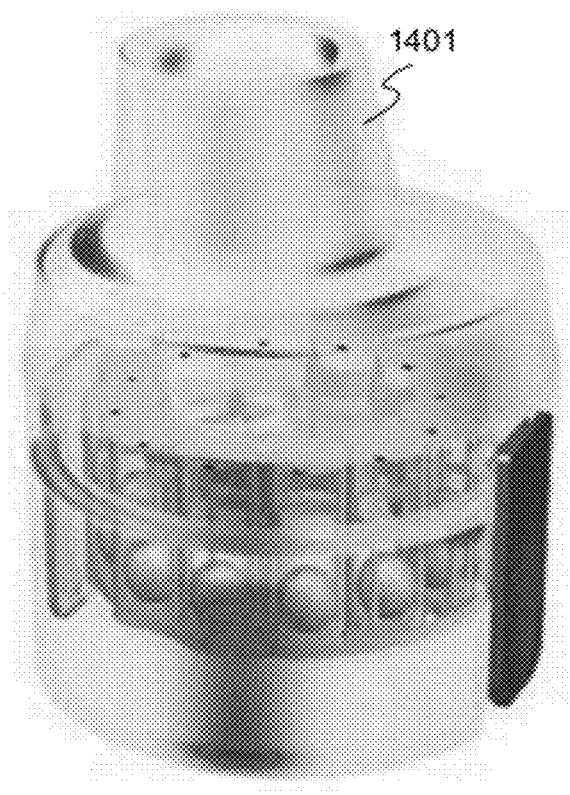

FIG. 14 illustrates multi-dose inhaler 1300 after loading. Once multi-dose inhaler 1300 is loaded, the user can rotate carriage 1303 to position a fresh cartridge 1000 in line with outlet 1401, and inhale air through inhaler 1300. To receive another dose of medicament, the user repeats the process with another fresh cartridge 1000.

Performance Examples

Tests have shown that devices according to embodiments may still effectively deliver medicament, even at low air flow rates, as compared with previous devices. Table 4 below compares the respirable fraction of particles produced by a DPI embodying the invention with that produced by a conventional inhaler using lactose carrier particles. Two different medicaments commonly prescribed for pulmonary disease were tested, the corticosteroid budesonide and the β-agonist salbutamol, at three different flow rates.

TABLE 4

Comparison of respirable fraction produced by embodiments of the present invention with prior lactose-based delivery

| Drug | Flow Rate ($L\,m^{-1}$) | Fine Particle Fraction (loaded) | |
|---|---|---|---|
| | | Lactose Standard | Present Invention |
| Budesonide | 45 | 28% | 58% |
| | 30 | 26% | 53% |
| | 15 | 5% | 24% |
| Salbutamol | 45 | 47% | 67% |
| | 30 | 46% | 68% |
| | 15 | 8% | 45% |

The relative insensitivity to flow rate may be especially important in the treatment of patients having compromised breathing ability, for example as a result of chronic obstructive pulmonary disease (COPD), which may make it difficult to use prior inhalers.

Testing has also shown that a DPI embodying the invention can include coatings of a wide variety of medications in doses comparable to those delivered by prior commercial inhalers. These doses may range from low doses (for example the 12 mcg of formoterol delivered by the Foradil Aerolizer and 22 mcg of tiotropium bromide delivered by the Spiriva Handihaler) to higher doses (for example 200 mcg of budesonide delivered from the Pulmicort Turbuhaler DPI, or 500 mcg fluticasone delivered by the Advair Diskus DPI).

In another comparison test, the performance of a dual-chamber DPI embodying the inventions was compared with the performance of a prior commercial inhaler of a different design, in dispensing two different medicaments, fluticasone propionate and salmeterol xinafoate. Each of the two actuators in the DPI embodying the invention was coated with one of the two medicaments. The test results are shown in Tables 5A and 5B below. Table 5A lists results for the prior commercial inhaler, and Table 5B lists results for the DPI embodying the invention.

TABLE 5A

Prior Commercial Inhaler Measured Performance

| Pressure Drop | Fluticasone Propionate | | | | Salmeterol | | | |
|---|---|---|---|---|---|---|---|---|
| | EF (%) | FPF (%) | RF (%) | FPD (mcg) | EF (%) | FPF (%) | RF (%) | FPD (mcg) |
| 4 kPa | 100.2 (1.5) | 21.8 (0.9) | 21.8 (0.8) | 54.6 (2.0) | 108.1 (5.1) | 16.7 (0.9) | 18.0 (0.5) | 9.0 (0.3) |
| 2 kPa | 94.2 (8.8) | 23.8 (3.4) | 22.3 (0.9) | 55.6 (2.4) | 108.2 (2.7) | 15.9 (0.6) | 17.2 (1.1) | 8.6 (0.5) |
| 1 kPa | 97.7 (5.0) | 16.2 (0.6) | 15.8 (0.8) | 39.5 (2.0) | 111.7 (6.3) | 13.8 (0.6) | 15.4 (1.5) | 8.4 (0.6) |

TABLE 5B

Dual Chamber DPI Embodying the Invention Measured Performance

| Pressure | Fluticasone Propionate | | | | Salmeterol | | | |
|---|---|---|---|---|---|---|---|---|
| Drop | EF (%) | FPF (%) | RF (%) | FPD (mcg) | EF (%) | FPF (%) | RF (%) | FPD (mcg) |
| 4 kPa | 65.2 (1.6) | 70.0 (2.7) | 45.7 (2.6) | 69.1 (6.6) | 56.6 (3.5) | 78.2 (3.4) | 45.5 (3.0) | 16.6 (1.7) |
| 2 kPa | 56.5 (0.3) | 70.8 (2.5) | 40.0 (1.4) | 66.2 (6.1) | 56.6 (4.3) | 72.1 (3.2) | 40.8 (4.2) | 15.0 (3.4) |
| 1 kPa | 48.1 (2.9) | 61.7 (0.6) | 29.7 (1.6) | 46.7 (2.5) | 42.9 (4.6) | 62.1 (5.6) | 26.5 (0.3) | 9.1 (1.5) |

In Tables 5A and 5B, emitted fraction (EF), fine particle fraction (FPF), respirable fraction (RF), and fine particle dose (FPD) values were determined in vitro for both inhalers. For the prior commercial inhaler, EF and RF are provided as the percentage of the labeled dose. All values are presented as mean (±standard deviation) for three replicates. As is apparent, the DPI embodying the invention provides a significantly higher medicament delivery, and also delivers significant doses of medicament at low flow rates. The relatively low values of FPF achieved by the prior commercial inhaler are believed to be due to the fact that a significant portion of the powdered medicament remained attached to the carrier particles used in that system, and did not emerge in respirable particle sizes. By contrast, in the DPI embodying the invention, only the powdered medicament, without carrier particles, emerges from the DPI, and thus a much larger percentage of the emitted medicament is respirable.

In another comparison test, two adult human volunteer subjects were re-enrolled from a cohort of subjects who participated in a safety study of inhaled Tacrolimus via nebulization (5 mg). Peak blood Tacrolimus concentrations 1 hr post-inhalation in subjects exposed to drug by nebulization ranged from 5 to 8 ng/ml. In the current study, subjects inhaled Tacrolimus via a DPI embodying the invention or HandiHaler DPI standard on study days 1 or 8, respectively. Tacrolimus levels were measured from blood samples 1 hr post-inhalation. The results from this study are summarized in Table 6 below.

TABLE 6

Comparison of blood level of Tacrolimus

| DPI | Drug | Ex-cipients | Total Powder (µg) | Fine Particle Fraction (loaded) (%) | Drug Level 1 hr Post-Inhalation (ng/ml) |
|---|---|---|---|---|---|
| HandiHaler | Tacrolimus | Yes | 2000 | 32 ± 3 | 7.7-10.0 |
| DPI Embodying Invention | Tacrolimus | No (pure) | 1095 ± 123 | 68 ± 2 | 14.2-15.5 |

It is to be understood that any workable combination of any features described herein is also considered to be disclosed. The invention has now been described in detail for the purposes of clarity and understanding. However, those skilled in the art will appreciate that certain changes and modifications may be practiced within the scope of the appended claims.

What is claimed is:

1. A dry powder inhaler, comprising:
   an inlet channel through which air enters the inhaler;
   a chamber that receives air from the inlet channel, wherein the chamber has a longitudinal axis, and wherein the inlet channel is generally co-axial with the longitudinal axis;
   a single bead-like actuator disposed within the chamber, wherein the bead-like actuator has an outer surface to which a medicament is adhered; and
   an outlet channel through which air and the powdered medicament leave the inhaler to be delivered to a patient, wherein the outlet channel is generally co-axial with the longitudinal axis of the chamber;
   wherein the geometry of the inhaler is such that a flow profile is generated within the chamber that causes the bead-like actuator to oscillate generally co-axial with the longitudinal axis, thus detaching the medicament from the outer surface of the bead-like actuator to be entrained by the air and delivered to the patient through the outlet channel.

2. The dry powder inhaler of claim 1, wherein the bead-like actuator comprises expanded polystyrene.

3. The dry powder inhaler of claim 1, wherein the bead-like actuator comprises polyolefin.

4. The dry powder inhaler of claim 1, wherein the bead-like actuator has a density between 0.001 and 5.0 g/cm3.

5. The dry powder inhaler of claim 1, wherein the bead-like actuator has a diameter of at least 500 microns.

6. The dry powder inhaler of claim 1, wherein the bead-like actuator has a diameter between about 1,000 and 25,000 microns.

7. The dry powder inhaler of claim 1, wherein a combination of medicaments is adhered to the bead-like actuator.

8. The dry powder inhaler of claim 1, further comprising a plurality of chambers disposed on a rotary element for selectively aligning any of the chambers with the outlet channel.

9. The dry powder inhaler of claim 1, wherein the inhaler includes multiple chambers, and wherein each chamber includes a bead-like actuator with a medicament.

10. The dry powder inhaler of claim 9, wherein a bead-like actuator in a first chamber has a medicament on it that is different from a medicament on a bead-like actuator in a second chamber.

11. The dry powder inhaler of claim 9, wherein at least one of the bead-like actuators includes multiple medicaments thereon.

12. A method, comprising:
   obtaining a dry power inhaler that includes an inlet channel, a chamber, and an outlet channel, the chamber holding a single bead-like actuator, wherein one or more powdered medicaments are adhered to an outside surface of the bead-like actuator; and
   inhaling through the outlet channel, causing air to flow into the inlet channel, through the chamber, and through the outlet chamber, the flowing air also causing the bead-like actuator to oscillate generally along a longitudinal axis extending between the inlet channel and the outlet channel to dislodge powdered medicament from the surface of the bead-like actuator to be entrained in the flowing air and carried through the outlet channel.

13. The method of claim 12, further comprising:
separating or opening portions of the inhaler comprising the chamber and the outlet channel;
loading the bead-like actuator into the chamber; and
re-engaging or closing the two portions of the inhaler.

14. The method of claim 12, wherein a combination of powdered medicaments is adhered to the bead-like actuator.

15. The method of claim 12, wherein the dry powder inhaler includes at least two chambers holding at least one bead-like actuator in each chamber, wherein the bead-like actuators each have medicament adhered to them, and wherein the flowing air causes each bead-like actuator to oscillate to dislodge powdered medicament to be inhaled.

16. The method of claim 15, wherein the bead-like actuators each have the same powdered medicament adhered thereto.

17. The method of claim 15, wherein the bead-like actuator in each chamber have a powdered medicament adhered thereto that are different from each other.

18. A dry powder inhaler, comprising:
an inlet channel through which air enters the inhaler;
a chamber that receives air from the inlet channel, wherein the chamber has a longitudinal axis;
a single bead-like actuator disposed within the chamber, wherein the bead-like actuator has an outer surface to which at least one medicament is adhered; and
an outlet channel through which air and the powdered medicament leave the inhaler to be delivered to a patient, wherein the inlet chamber and the outlet chamber are aligned with the longitudinal axis;
wherein the geometry of the inlet and the chamber, and the mass of the bead-like actuator, are configured such that the bead-like actuator oscillates at a desired frequency and amplitude within the chamber when fluid flows through the chamber in order to detach the medicament from the outer surface of the bead-like actuator to be delivered to the patient through the outlet channel.

* * * * *